US008728147B2

(12) United States Patent
Brown

(10) Patent No.: US 8,728,147 B2
(45) Date of Patent: May 20, 2014

(54) LONGITUDINALLY FLEXIBLE EXPANDABLE STENT

(75) Inventor: Brian J. Brown, Hanover, MN (US)

(73) Assignee: Boston Scientific Limited, Maple Grove, MN (US)

( * ) Notice: Subject to any disclaimer, the term of this patent is extended or adjusted under 35 U.S.C. 154(b) by 0 days.

(21) Appl. No.: 13/332,025

(22) Filed: Dec. 20, 2011

(65) Prior Publication Data

US 2012/0143309 A1 Jun. 7, 2012

Related U.S. Application Data

(63) Continuation of application No. 13/195,581, filed on Aug. 1, 2011, now abandoned, which is a continuation of application No. 10/705,273, filed on Nov. 10, 2003, now Pat. No. 7,988,717, which is a continuation of application No. 09/197,278, filed on Nov. 20, 1998, now Pat. No. 7,204,848, which is a continuation-in-part of application No. 08/511,076, filed on Aug. 3, 1995, now Pat. No. 6,818,014, which is a continuation-in-part of application No. 08/396,569, filed on Mar. 1, 1995, now abandoned, said application No. 13/195,581 is a continuation of application No. 10/800,572, filed on Mar. 15, 2004, now Pat. No. 8,114,146, which is a continuation of application No. 09/197,278, filed on Nov. 20, 1998, now Pat. No. 7,204,848, which is a continuation-in-part of application No. 08/511,076, filed on Aug. 3, 1995, now Pat. No. 6,818,014, which is a continuation-in-part of application No. 08/396,569, filed on Mar. 1, 1995, now abandoned.

(51) Int. Cl.
*A61F 2/06* (2013.01)

(52) U.S. Cl.
USPC .......................... 623/1.22; 623/1.18; 623/1.2

(58) Field of Classification Search
USPC ......................................... 623/1.16, 1.2, 1.22
See application file for complete search history.

(56) References Cited

U.S. PATENT DOCUMENTS 2,316,286 A 4/1943 Raney
2,836,181 A 5/1958 Trapp
(Continued)

FOREIGN PATENT DOCUMENTS

DE 1766921 1/1970
DE 4032759 4/1992
(Continued)

OTHER PUBLICATIONS

U.S. District Court for the District of Massachusetts; Orbusneich Medical Co. Ltd., BVI's and Orbusneich Medical, Inc.'s Opening Claim Construction Brief; *Orbusneich Medical Co. Ltd., BVI and Orbusneich Medical, Inc. v. Boston Scientific Corporation*; Jan. 10, 2011; Case No. C.A. No. 1:09-cv-10962 (RGS), pp. 1-36.

(Continued)

*Primary Examiner* — Thomas J Sweet
*Assistant Examiner* — Brian Dukert
(74) *Attorney, Agent, or Firm* — Frommer Lawrence & Haug LLP; William F. Lawrence, Esq.; Stephen J. Lieb

(57) ABSTRACT

Segmented articulatable stent of open structure comprised of end-connected struts of first and second lengths making up first and second segments with angular interconnects between adjacent first and second segments.

30 Claims, 18 Drawing Sheets

(56) References Cited

U.S. PATENT DOCUMENTS

| | | |
|---|---|---|
| 3,105,492 A | 10/1963 | Jeckel |
| 3,272,204 A | 9/1966 | Artandi et al. |
| 3,490,975 A | 1/1970 | Lightwood et al. |
| 3,509,883 A | 5/1970 | Dibelius |
| 3,526,228 A | 9/1970 | Lyng |
| 3,562,820 A | 2/1971 | Braun |
| 3,635,215 A | 1/1972 | Shea et al. |
| 3,657,744 A | 4/1972 | Ersek |
| 3,771,526 A | 11/1973 | Rudie |
| 3,868,956 A | 3/1975 | Alfidi et al. |
| 3,993,078 A | 11/1976 | Bergentz et al. |
| 4,078,167 A | 3/1978 | Banas et al. |
| 4,127,761 A | 11/1978 | Pauley et al. |
| 4,130,904 A | 12/1978 | Whalen |
| 4,140,126 A | 2/1979 | Choudhury |
| 4,141,364 A | 2/1979 | Schultze |
| 4,164,045 A | 8/1979 | Bokros et al. |
| 4,214,587 A | 7/1980 | Sakura, Jr. et al. |
| 4,300,244 A | 11/1981 | Bokros |
| 4,313,231 A | 2/1982 | Koyamada |
| 4,319,363 A | 3/1982 | Ketharanathan |
| 4,413,629 A | 11/1983 | Durley, III |
| 4,425,908 A | 1/1984 | Simon |
| 4,441,215 A | 4/1984 | Kaster |
| 4,464,722 A | 8/1984 | Von Osten |
| 4,470,407 A | 9/1984 | Hussein |
| 4,501,264 A | 2/1985 | Rockey |
| 4,503,569 A | 3/1985 | Dotter |
| 4,512,338 A | 4/1985 | Balko et al. |
| 4,535,770 A | 8/1985 | Lemole |
| 4,550,447 A | 11/1985 | Seiler, Jr. et al. |
| 4,553,545 A | 11/1985 | Maass et al. |
| 4,560,374 A | 12/1985 | Hammerslag |
| 4,580,568 A | 4/1986 | Gianturco |
| 4,597,389 A | 7/1986 | Ibrahim et al. |
| 4,647,416 A | 3/1987 | Seiler, Jr. et al. |
| 4,649,922 A | 3/1987 | Wiktor |
| 4,655,771 A | 4/1987 | Wallsten |
| 4,655,776 A | 4/1987 | Lesinski |
| 4,665,906 A | 5/1987 | Jervis |
| 4,665,918 A | 5/1987 | Garza et al. |
| 4,681,110 A | 7/1987 | Wiktor |
| 4,693,721 A | 9/1987 | Ducheyne |
| 4,733,665 A | 3/1988 | Palmaz |
| 4,739,762 A | 4/1988 | Palmaz |
| 4,740,207 A | 4/1988 | Kreamer |
| 4,760,849 A | 8/1988 | Kropf |
| 4,762,128 A | 8/1988 | Rosenbluth |
| 4,768,507 A | 9/1988 | Fischell et al. |
| 4,769,029 A | 9/1988 | Patel |
| 4,771,773 A | 9/1988 | Kropf |
| 4,776,337 A | 10/1988 | Palmaz |
| 4,787,899 A | 11/1988 | Lazarus |
| 4,795,458 A | 1/1989 | Regan |
| 4,795,465 A | 1/1989 | Marten |
| 4,800,882 A | 1/1989 | Gianturco |
| 4,820,298 A | 4/1989 | Leveen et al. |
| 4,830,003 A | 5/1989 | Wolff et al. |
| 4,842,575 A | 6/1989 | Hoffman et al. |
| 4,848,343 A | 7/1989 | Wallsten et al. |
| 4,851,009 A | 7/1989 | Pinchuk |
| 4,856,516 A | 8/1989 | Hillstead |
| 4,872,874 A | 10/1989 | Taheri |
| 4,877,030 A | 10/1989 | Beck et al. |
| 4,878,906 A | 11/1989 | Lindemann et al. |
| 4,885,002 A | 12/1989 | Watanabe et al. |
| 4,886,062 A | 12/1989 | Wiktor |
| 4,913,141 A | 4/1990 | Hillstead |
| 4,922,905 A | 5/1990 | Strecker |
| 4,950,227 A | 8/1990 | Savin et al. |
| 4,950,258 A | 8/1990 | Kawai et al. |
| 4,983,167 A | 1/1991 | Sahota |
| 4,994,071 A | 2/1991 | MacGregor |
| 5,011,472 A | 4/1991 | Aebischer et al. |
| 5,015,253 A | 5/1991 | MacGregor |
| 5,019,090 A | 5/1991 | Pinchuk |
| 5,035,706 A | 7/1991 | Gianturco et al. |
| 5,037,392 A | 8/1991 | Hillstead |
| 5,059,211 A | 10/1991 | Stack et al. |
| 5,064,435 A | 11/1991 | Porter |
| 5,071,407 A | 12/1991 | Termin et al. |
| 5,089,005 A | 2/1992 | Harada |
| 5,091,205 A | 2/1992 | Fan |
| 5,091,211 A | 2/1992 | Richard |
| 5,092,877 A | 3/1992 | Pinchuk |
| 5,100,429 A | 3/1992 | Sinofsky et al. |
| 5,102,417 A | 4/1992 | Palmaz |
| 5,104,399 A | 4/1992 | Lazarus |
| 5,104,404 A | 4/1992 | Wolff |
| 5,108,415 A | 4/1992 | Pinchuk et al. |
| 5,108,417 A | 4/1992 | Sawyer |
| 5,122,154 A | 6/1992 | Rhodes |
| 5,123,917 A | 6/1992 | Lee |
| 5,133,732 A | 7/1992 | Wiktor |
| 5,135,536 A | 8/1992 | Hillstead |
| 5,139,480 A | 8/1992 | Hickle et al. |
| 5,147,385 A | 9/1992 | Beck et al. |
| 5,147,400 A | 9/1992 | Kaplan et al. |
| 5,158,548 A | 10/1992 | Lau et al. |
| 5,163,952 A | 11/1992 | Froix |
| 5,183,085 A | 2/1993 | Timmermans |
| 5,195,984 A | 3/1993 | Schatz |
| 5,197,978 A | 3/1993 | Hess |
| 5,217,483 A | 6/1993 | Tower |
| 5,226,913 A | 7/1993 | Pinchuk |
| 5,282,823 A | 2/1994 | Schwartz et al. |
| 5,282,824 A | 2/1994 | Gianturco |
| 5,290,305 A | 3/1994 | Inoue |
| 5,292,331 A | 3/1994 | Boneau |
| 5,304,121 A | 4/1994 | Sahatjian |
| 5,304,200 A | 4/1994 | Spaulding |
| 5,314,472 A | 5/1994 | Fontaine |
| 5,344,425 A | 9/1994 | Sawyer |
| 5,354,308 A | 10/1994 | Simon et al. |
| 5,354,309 A | 10/1994 | Shepp-Pesch et al. |
| 5,356,423 A | 10/1994 | Tihon et al. |
| 5,370,683 A | 12/1994 | Fontaine |
| 5,382,261 A | 1/1995 | Palmaz |
| 5,383,892 A | 1/1995 | Cardon et al. |
| 5,389,106 A | 2/1995 | Tower |
| 5,395,390 A | 3/1995 | Simon et al. |
| 5,397,355 A | 3/1995 | Marin et al. |
| 5,405,377 A | 4/1995 | Cragg |
| 5,411,552 A | 5/1995 | Andersen et al. |
| 5,443,498 A | 8/1995 | Fontaine |
| 5,449,373 A | 9/1995 | Pinchasik et al. |
| 5,465,011 A | 11/1995 | Miller et al. |
| 5,474,547 A | 12/1995 | Aebischer et al. |
| 5,507,767 A | 4/1996 | Maeda et al. |
| 5,514,154 A | 5/1996 | Lau et al. |
| 5,527,354 A | 6/1996 | Fontaine et al. |
| 5,545,210 A | 8/1996 | Hess et al. |
| 5,549,663 A | 8/1996 | Cottone, Jr. |
| 5,554,181 A | 9/1996 | Das |
| 5,562,922 A | 10/1996 | Lambert |
| 5,569,295 A | 10/1996 | Lam |
| 5,591,197 A | 1/1997 | Orth et al. |
| 5,591,227 A | 1/1997 | Dinh et al. |
| 5,591,230 A | 1/1997 | Horn et al. |
| 5,593,442 A | 1/1997 | Klein |
| 5,599,352 A | 2/1997 | Dinh et al. |
| 5,609,627 A | 3/1997 | Goicoechea et al. |
| 5,613,981 A | 3/1997 | Boyle et al. |
| 5,617,878 A | 4/1997 | Taheri |
| 5,624,411 A | 4/1997 | Tuch |
| 5,630,829 A | 5/1997 | Lauterjung |
| 5,643,312 A | 7/1997 | Fischell et al. |
| 5,649,952 A | 7/1997 | Lam |
| 5,653,727 A | 8/1997 | Wiktor |
| 5,667,523 A | 9/1997 | Bynon et al. |
| 5,674,241 A | 10/1997 | Bley et al. |
| 5,679,400 A | 10/1997 | Tuch |
| 5,683,450 A | 11/1997 | Goicoechea et al. |
| 5,693,088 A | 12/1997 | Lazarus |

(56) References Cited

U.S. PATENT DOCUMENTS

| | | |
|---|---|---|
| 5,695,516 A | 12/1997 | Fischell et al. |
| 5,697,971 A | 12/1997 | Fischell et al. |
| 5,700,285 A | 12/1997 | Myers et al. |
| 5,707,386 A | 1/1998 | Schnepp-Pesch et al. |
| 5,716,365 A | 2/1998 | Goicoechea et al. |
| 5,716,393 A | 2/1998 | Lindenberg et al. |
| 5,716,396 A | 2/1998 | Williams, Jr. |
| 5,718,713 A | 2/1998 | Frantzen |
| 5,718,724 A | 2/1998 | Goicoechea et al. |
| 5,722,412 A | 3/1998 | Pflugrath et al. |
| 5,725,572 A | 3/1998 | Lam et al. |
| 5,728,158 A | 3/1998 | Lau et al. |
| 5,733,303 A | 3/1998 | Israel et al. |
| 5,733,325 A | 3/1998 | Robinson et al. |
| 5,735,871 A | 4/1998 | Sgro |
| 5,735,892 A | 4/1998 | Myers et al. |
| 5,735,893 A | 4/1998 | Lau et al. |
| 5,741,327 A | 4/1998 | Frantzen |
| 5,741,333 A | 4/1998 | Frid |
| 5,749,880 A | 5/1998 | Banas et al. |
| 5,755,770 A | 5/1998 | Ravenscroft |
| 5,755,771 A | 5/1998 | Penn et al. |
| 5,755,776 A | 5/1998 | Al-Saadon |
| 5,755,781 A | 5/1998 | Jayaraman |
| 5,759,192 A | 6/1998 | Saunders |
| 5,776,161 A | 7/1998 | Globerman |
| 5,776,180 A | 7/1998 | Goicoechea et al. |
| 5,776,183 A | 7/1998 | Kanesaka et al. |
| 5,800,508 A | 9/1998 | Goicoechea et al. |
| 5,800,514 A | 9/1998 | Nunez et al. |
| 5,800,515 A | 9/1998 | Nadal et al. |
| 5,800,519 A | 9/1998 | Sandock |
| 5,800,520 A | 9/1998 | Fogarty et al. |
| 5,800,521 A | 9/1998 | Orth |
| 5,800,524 A | 9/1998 | Borghi |
| 5,807,404 A * | 9/1998 | Richter ............... 623/1.16 |
| 5,810,872 A | 9/1998 | Kanesaka et al. |
| 5,817,404 A | 10/1998 | Kawakita et al. |
| 5,824,040 A | 10/1998 | Cox et al. |
| 5,824,043 A | 10/1998 | Cottone, Jr. |
| 5,824,045 A | 10/1998 | Alt |
| 5,824,046 A | 10/1998 | Smith et al. |
| 5,824,048 A | 10/1998 | Tuch |
| 5,824,059 A | 10/1998 | Wijay |
| 5,827,321 A | 10/1998 | Roubin et al. |
| 5,836,966 A | 11/1998 | St. Germain |
| 5,843,117 A | 12/1998 | Alt et al. |
| 5,843,120 A | 12/1998 | Israel et al. |
| 5,843,158 A | 12/1998 | Lenker et al. |
| 5,843,164 A | 12/1998 | Frantzen et al. |
| 5,843,175 A | 12/1998 | Frantzen |
| 5,846,246 A | 12/1998 | Dirks et al. |
| 5,853,419 A | 12/1998 | Imran |
| 5,855,597 A | 1/1999 | Jayaraman |
| 5,855,600 A | 1/1999 | Alt |
| 5,860,999 A | 1/1999 | Schnepp-Pesch et al. |
| 5,861,025 A | 1/1999 | Boudghene et al. |
| 5,868,780 A | 2/1999 | Lashinski et al. |
| 5,868,782 A | 2/1999 | Frantzen |
| 5,873,906 A | 2/1999 | Lau et al. |
| 5,876,432 A | 3/1999 | Lau et al. |
| 5,876,449 A | 3/1999 | Starck et al. |
| 5,879,381 A | 3/1999 | Moriuchi et al. |
| 5,882,335 A | 3/1999 | Leone et al. |
| 5,886,062 A | 3/1999 | Dietrich et al. |
| 5,893,363 A | 4/1999 | Little et al. |
| 5,895,406 A | 4/1999 | Gray et al. |
| 5,895,407 A | 4/1999 | Jayaraman |
| 5,897,588 A | 4/1999 | Hull et al. |
| 5,897,589 A | 4/1999 | Cottenceau et al. |
| 5,900,246 A | 5/1999 | Lambert |
| 5,902,317 A | 5/1999 | Kleshinski et al. |
| 5,902,332 A | 5/1999 | Schatz |
| 5,911,732 A | 6/1999 | Hojeibane |
| 5,911,754 A | 6/1999 | Kanesaka et al. |
| 5,913,895 A | 6/1999 | Burpee et al. |
| 5,913,897 A | 6/1999 | Corso, Jr. et al. |
| 5,916,263 A | 6/1999 | Goicoechea et al. |
| 5,922,021 A | 7/1999 | Jang |
| 5,925,061 A | 7/1999 | Ogi et al. |
| 5,928,279 A | 7/1999 | Shannon et al. |
| 5,928,280 A | 7/1999 | Hansen et al. |
| 5,935,161 A | 8/1999 | Robinson et al. |
| 5,935,162 A | 8/1999 | Dang |
| 5,938,682 A | 8/1999 | Hojeibane et al. |
| 5,938,696 A | 8/1999 | Goicoechea et al. |
| 5,938,697 A | 8/1999 | Killion et al. |
| 5,948,016 A | 9/1999 | Jang |
| 5,951,586 A | 9/1999 | Berg et al. |
| 5,954,743 A | 9/1999 | Jang |
| 5,957,930 A | 9/1999 | Vrba |
| 5,961,545 A | 10/1999 | Lentz et al. |
| 5,964,798 A | 10/1999 | Imran |
| 5,972,018 A | 10/1999 | Israel et al. |
| 5,980,552 A | 11/1999 | Pinchasik et al. |
| 5,980,553 A | 11/1999 | Gray et al. |
| 5,984,016 A | 11/1999 | Samuelsson |
| 6,001,125 A | 12/1999 | Golds et al. |
| 6,013,854 A | 1/2000 | Moriuchi |
| 6,017,363 A | 1/2000 | Hojeibane |
| 6,017,365 A | 1/2000 | Von Oepen |
| 6,019,789 A | 2/2000 | Dinh et al. |
| 6,022,370 A | 2/2000 | Tower |
| 6,027,526 A | 2/2000 | Limon et al. |
| 6,027,527 A | 2/2000 | Asano et al. |
| 6,033,433 A | 3/2000 | Ehr et al. |
| 6,039,756 A | 3/2000 | Jang |
| 6,042,597 A | 3/2000 | Kveen et al. |
| 6,051,020 A | 4/2000 | Goicoechea et al. |
| 6,053,940 A | 4/2000 | Wijay |
| 6,053,941 A | 4/2000 | Lindenberg et al. |
| 6,056,775 A | 5/2000 | Borghi et al. |
| 6,059,811 A | 5/2000 | Pinchasik et al. |
| 6,059,822 A | 5/2000 | Kanesaka et al. |
| 6,068,656 A | 5/2000 | Von Oepen |
| 6,083,259 A | 7/2000 | Frantzen |
| 6,090,127 A | 7/2000 | Globerman |
| 6,099,561 A | 8/2000 | Alt |
| 6,106,548 A | 8/2000 | Roubin et al. |
| 6,113,627 A | 9/2000 | Jang |
| 6,117,165 A | 9/2000 | Becker |
| 6,120,522 A | 9/2000 | Vrba et al. |
| 6,123,712 A | 9/2000 | Di Caprio et al. |
| 6,123,721 A | 9/2000 | Jang |
| 6,124,523 A | 9/2000 | Banas et al. |
| 6,129,755 A | 10/2000 | Mathis et al. |
| 6,132,460 A | 10/2000 | Thompson |
| 6,132,461 A | 10/2000 | Thompson |
| 6,133,627 A | 10/2000 | Khandros et al. |
| 6,136,023 A | 10/2000 | Boyle |
| 6,139,573 A | 10/2000 | Sogard et al. |
| 6,152,957 A | 11/2000 | Jang |
| 6,156,052 A | 12/2000 | Richter et al. |
| 6,159,237 A | 12/2000 | Alt et al. |
| 6,159,238 A | 12/2000 | Killion et al. |
| 6,162,243 A | 12/2000 | Gray et al. |
| 6,171,334 B1 | 1/2001 | Cox |
| 6,174,326 B1 | 1/2001 | Kitaoka et al. |
| 6,179,867 B1 | 1/2001 | Cox |
| 6,179,868 B1 | 1/2001 | Burpee et al. |
| 6,183,506 B1 | 2/2001 | Penn et al. |
| 6,187,034 B1 | 2/2001 | Frantzen |
| 6,190,403 B1 | 2/2001 | Fischell et al. |
| 6,193,744 B1 | 2/2001 | Ehr et al. |
| 6,193,747 B1 | 2/2001 | Von Oepen |
| 6,200,334 B1 | 3/2001 | Jang |
| 6,200,337 B1 | 3/2001 | Moriuchi et al. |
| 6,203,569 B1 | 3/2001 | Wijay |
| 6,206,911 B1 | 3/2001 | Milo |
| 6,217,608 B1 | 4/2001 | Penn et al. |
| 6,231,598 B1 | 5/2001 | Berry et al. |
| 6,235,053 B1 | 5/2001 | Jang |
| 6,238,409 B1 | 5/2001 | Hojeibane |
| 6,238,430 B1 | 5/2001 | Klumb et al. |

(56) References Cited

U.S. PATENT DOCUMENTS

| | | |
|---|---|---|
| 6,241,039 B1 | 6/2001 | Jarnstrom et al. |
| 6,241,760 B1 | 6/2001 | Jang |
| 6,241,762 B1 | 6/2001 | Shanley |
| 6,245,101 B1 | 6/2001 | Drasler et al. |
| 6,245,102 B1 | 6/2001 | Jayaraman |
| 6,254,628 B1 | 7/2001 | Wallace et al. |
| 6,254,632 B1 | 7/2001 | Wu et al. |
| 6,261,319 B1 | 7/2001 | Kveen et al. |
| 6,264,689 B1 | 7/2001 | Colgan et al. |
| 6,270,524 B1 | 8/2001 | Kim |
| 6,273,910 B1 | 8/2001 | Limon |
| 6,273,911 B1 | 8/2001 | Cox et al. |
| 6,309,414 B1 | 10/2001 | Rolando et al. |
| 6,319,277 B1 | 11/2001 | Rudnick et al. |
| 6,331,188 B1 | 12/2001 | Lau et al. |
| 6,331,189 B1 | 12/2001 | Wolinsky et al. |
| 6,340,366 B2 | 1/2002 | Wijay |
| 6,342,067 B1 | 1/2002 | Mathis et al. |
| 6,348,065 B1 | 2/2002 | Brown et al. |
| 6,350,277 B1 | 2/2002 | Kocur |
| 6,352,552 B1 | 3/2002 | Levinson et al. |
| 6,355,057 B1 | 3/2002 | DeMarais et al. |
| 6,355,059 B1 | 3/2002 | Richter et al. |
| 6,355,063 B1 | 3/2002 | Calcote |
| 6,358,274 B1 | 3/2002 | Thompson |
| 6,361,759 B1 | 3/2002 | Frayne et al. |
| 6,364,903 B2 | 4/2002 | Tseng et al. |
| 6,364,904 B1 | 4/2002 | Smith |
| 6,375,677 B1 | 4/2002 | Penn et al. |
| 6,379,379 B1 | 4/2002 | Wang |
| 6,379,382 B1 | 4/2002 | Yang |
| 6,383,214 B1 | 5/2002 | Banas et al. |
| 6,387,122 B1 | 5/2002 | Cragg |
| 6,395,020 B1 | 5/2002 | Ley et al. |
| 6,395,212 B1 | 5/2002 | Solem |
| 6,398,803 B1 | 6/2002 | Layne et al. |
| 6,398,805 B1 | 6/2002 | Alt |
| 6,409,753 B1 | 6/2002 | Brown et al. |
| 6,409,761 B1 | 6/2002 | Jang |
| 6,416,538 B1 | 7/2002 | Ley et al. |
| 6,416,543 B1 | 7/2002 | Hilaire et al. |
| 6,423,090 B1 | 7/2002 | Hancock |
| 6,423,091 B1 | 7/2002 | Hojeibane |
| 6,432,132 B1 | 8/2002 | Cottone et al. |
| 6,432,133 B1 | 8/2002 | Lau et al. |
| 6,443,982 B1 | 9/2002 | Israel et al. |
| 6,451,047 B2 | 9/2002 | McCrea et al. |
| 6,451,049 B2 | 9/2002 | Vallana et al. |
| 6,451,052 B1 | 9/2002 | Burmeister et al. |
| 6,461,380 B1 | 10/2002 | Cox |
| 6,461,381 B2 | 10/2002 | Israel et al. |
| 6,464,720 B2 | 10/2002 | Boatman et al. |
| 6,464,722 B2 | 10/2002 | Israel |
| 6,468,302 B2 | 10/2002 | Cox et al. |
| 6,471,720 B1 | 10/2002 | Ehr et al. |
| 6,475,235 B1 | 11/2002 | Jayaraman |
| 6,475,236 B1 | 11/2002 | Roubin et al. |
| 6,478,816 B1 | 11/2002 | Kveen et al. |
| 6,485,508 B1 | 11/2002 | McGuinness |
| 6,485,509 B2 | 11/2002 | Killion et al. |
| 6,488,700 B2 | 12/2002 | Klumb et al. |
| 6,488,701 B1 | 12/2002 | Nolting et al. |
| 6,488,703 B1 | 12/2002 | Kveen et al. |
| 6,503,270 B1 | 1/2003 | Richter et al. |
| 6,506,201 B2 | 1/2003 | DiCaprio et al. |
| 6,506,211 B1 | 1/2003 | Skubitz et al. |
| 6,508,834 B1 | 1/2003 | Pinchasik et al. |
| 6,511,505 B2 | 1/2003 | Cox et al. |
| 6,514,283 B2 | 2/2003 | DiMatteo et al. |
| 6,520,984 B1 | 2/2003 | Garrison et al. |
| 6,520,987 B1 | 2/2003 | Plante |
| 6,533,808 B1 | 3/2003 | Thompson |
| 6,533,809 B2 | 3/2003 | Von Oepen |
| 6,540,774 B1 | 4/2003 | Cox |
| 6,540,775 B1 | 4/2003 | Fischell et al. |
| 6,540,777 B2 | 4/2003 | Stenzel |
| 6,547,814 B2 | 4/2003 | Edwin et al. |
| 6,547,815 B2 | 4/2003 | Myers |
| 6,551,350 B1 | 4/2003 | Thornton et al. |
| 6,558,414 B2 | 5/2003 | Layne |
| 6,558,415 B2 | 5/2003 | Thompson |
| 6,569,193 B1 | 5/2003 | Cox et al. |
| 6,579,314 B1 | 6/2003 | Lombardi et al. |
| 6,582,461 B1 | 6/2003 | Burmeister et al. |
| 6,589,276 B2 | 7/2003 | Pinchasik et al. |
| 6,596,022 B2 | 7/2003 | Lau et al. |
| 6,602,285 B1 | 8/2003 | Von Oepen |
| 6,605,110 B2 | 8/2003 | Harrison |
| 6,610,086 B1 | 8/2003 | Kock et al. |
| 6,613,081 B2 | 9/2003 | Kim et al. |
| 6,616,688 B2 | 9/2003 | Von Oepen |
| 6,620,201 B1 | 9/2003 | Nadal et al. |
| 6,635,084 B2 | 10/2003 | Israel et al. |
| 6,652,579 B1 | 11/2003 | Cox et al. |
| 6,669,723 B2 | 12/2003 | Killion |
| 6,673,107 B1 | 1/2004 | Brandt et al. |
| 6,679,911 B2 | 1/2004 | Burgermeister |
| 6,682,554 B2 | 1/2004 | Von Oepen et al. |
| 6,709,453 B2 | 3/2004 | Pinchasik et al. |
| 6,723,119 B2 | 4/2004 | Pinchasik et al. |
| 6,730,116 B1 | 5/2004 | Wolinsky et al. |
| 6,730,117 B1 | 5/2004 | Tseng et al. |
| 6,733,524 B2 | 5/2004 | Tseng |
| 6,736,844 B1 | 5/2004 | Glatt et al. |
| 6,755,856 B2 | 6/2004 | Seibold et al. |
| 6,770,088 B1 | 8/2004 | Jang |
| 6,776,793 B2 | 8/2004 | Brown et al. |
| 6,818,014 B2 | 11/2004 | Brown et al. |
| 6,821,292 B2 | 11/2004 | Pazienza et al. |
| 6,854,172 B2 | 2/2005 | Kaese et al. |
| 6,875,228 B2 | 4/2005 | Pinchasik et al. |
| 6,887,264 B2 | 5/2005 | Penn et al. |
| 6,896,696 B2 | 5/2005 | Doran et al. |
| 6,913,619 B2 | 7/2005 | Brown et al. |
| 6,929,660 B1 | 8/2005 | Ainsworth et al. |
| 6,962,203 B2 | 11/2005 | Funchess |
| 6,962,603 B1 | 11/2005 | Brown et al. |
| 6,974,475 B1 | 12/2005 | Wall |
| 6,981,986 B1 | 1/2006 | Brown et al. |
| 7,025,777 B2 | 4/2006 | Moore |
| 7,044,961 B2 | 5/2006 | Lentz |
| 7,070,614 B1 | 7/2006 | Neuss et al. |
| 7,081,130 B2 | 7/2006 | Jang |
| 7,108,714 B1 | 9/2006 | Becker |
| 7,112,216 B2 | 9/2006 | Gregorich |
| 7,128,756 B2 | 10/2006 | Lowe |
| 7,131,993 B2 | 11/2006 | Gregorich |
| 7,179,285 B2 | 2/2007 | Ikeuchi et al. |
| 7,179,286 B2 | 2/2007 | Lenz |
| 7,204,848 B1 | 4/2007 | Brown et al. |
| 7,264,633 B2 | 9/2007 | Bonsignore |
| 7,329,277 B2 | 2/2008 | Addonizio et al. |
| 7,354,450 B2 | 4/2008 | Bicek |
| 7,404,823 B2 | 7/2008 | Gregorich et al. |
| 7,534,257 B2 | 5/2009 | Richter |
| 7,635,384 B2 | 12/2009 | Gregorich |
| 7,682,384 B2 | 3/2010 | Addonizio et al. |
| 7,763,011 B2 | 7/2010 | Ortiz et al. |
| 7,828,835 B2 | 11/2010 | Richter et al. |
| 7,842,081 B2 | 11/2010 | Yadin |
| 7,842,082 B2 | 11/2010 | Yadin |
| 7,942,922 B2 | 5/2011 | Addonizio et al. |
| 7,967,852 B2 | 6/2011 | Addonizio et al. |
| 7,985,251 B2 | 7/2011 | Ikeuchi |
| 7,988,720 B2 | 8/2011 | Brown et al. |
| 8,007,528 B2 | 8/2011 | Yadin |
| 2001/0020183 A1 | 9/2001 | Jang |
| 2001/0029397 A1 | 10/2001 | Thompson |
| 2001/0041930 A1 | 11/2001 | Globerman |
| 2001/0044650 A1 | 11/2001 | Simso |
| 2001/0056298 A1 | 12/2001 | Brown et al. |
| 2002/0019660 A1 | 2/2002 | Gianotti et al. |
| 2002/0042647 A1 | 4/2002 | Jang |
| 2002/0095206 A1 | 7/2002 | Addonizio |

(56) References Cited

U.S. PATENT DOCUMENTS

| | | |
|---|---|---|
| 2002/0095208 A1 | 7/2002 | Gregorich et al. |
| 2002/0103529 A1 | 8/2002 | Pinchasik et al. |
| 2002/0116044 A1 | 8/2002 | Cottone, Jr. et al. |
| 2002/0116049 A1 | 8/2002 | Girton et al. |
| 2002/0120327 A1 | 8/2002 | Cox |
| 2003/0033007 A1 | 2/2003 | Sirhan |
| 2003/0069633 A1 | 4/2003 | Richter |
| 2003/0225448 A1 | 12/2003 | Gerberding |
| 2004/0143318 A1 | 7/2004 | Tseng et al. |
| 2004/0230294 A1 | 11/2004 | Fischell |
| 2004/0243216 A1 | 12/2004 | Gregorich |
| 2005/0049687 A1 | 3/2005 | Yang et al. |
| 2006/0052864 A1 | 3/2006 | Harder |
| 2007/0073384 A1 | 3/2007 | Brown et al. |
| 2008/0065195 A1 | 3/2008 | Brown et al. |
| 2008/0065197 A1 | 3/2008 | Meyer |
| 2008/0281406 A1 | 11/2008 | Addonizio et al. |
| 2008/0281407 A1 | 11/2008 | Addonizio et al. |
| 2008/0288050 A1* | 11/2008 | Addonizio et al. .......... 623/1.22 |
| 2008/0288051 A1 | 11/2008 | Addonizio et al. |
| 2008/0288052 A1 | 11/2008 | Addonizio et al. |
| 2008/0288053 A1 | 11/2008 | Addonizio et al. |
| 2008/0294241 A1 | 11/2008 | Addonizio et al. |
| 2008/0294243 A1 | 11/2008 | Addonizio et al. |
| 2008/0294244 A1 | 11/2008 | Addonizio et al. |
| 2008/0319537 A1 | 12/2008 | Addonizio et al. |
| 2009/0024198 A1 | 1/2009 | Addonizio et al. |
| 2009/0024207 A1 | 1/2009 | Addonizio et al. |
| 2010/0211152 A1 | 8/2010 | Addonizio et al. |
| 2010/0324661 A1 | 12/2010 | Addonizio et al. |
| 2010/0324662 A1 | 12/2010 | Addonizio et al. |

FOREIGN PATENT DOCUMENTS

| | | |
|---|---|---|
| DE | 4303181 | 8/1994 |
| DE | 29608037 | 7/1996 |
| DE | 297 02 671 | 4/1997 |
| DE | 29701758 | 5/1997 |
| DE | 29702671 | 5/1997 |
| DE | 29708689 | 7/1997 |
| DE | 29708879 | 7/1997 |
| DE | 19614160 | 10/1997 |
| DE | 29716476 | 2/1998 |
| DE | 19717475 | 9/1998 |
| DE | 19722384 | 12/1998 |
| DE | 29816878 | 12/1998 |
| DE | 19834956 | 5/1999 |
| DE | 19822157 | 11/1999 |
| DE | 19840645 | 3/2000 |
| EP | 0045627 | 2/1982 |
| EP | 0177330 | 4/1986 |
| EP | 0183372 | 6/1986 |
| EP | 0221570 | 5/1987 |
| EP | 0274846 | 7/1988 |
| EP | 0282175 | 9/1988 |
| EP | 0312852 | 4/1989 |
| EP | 0335341 | 10/1989 |
| EP | 0364787 | 4/1990 |
| EP | 0421729 | 4/1991 |
| EP | 0435518 | 7/1991 |
| EP | 0540290 | 5/1993 |
| EP | 0541443 | 5/1993 |
| EP | 0556850 | 8/1993 |
| EP | 0565251 | 10/1993 |
| EP | 0566807 | 10/1993 |
| EP | 0587197 | 3/1994 |
| EP | 0606165 | 7/1994 |
| EP | 0617913 | 10/1994 |
| EP | 0645125 | 3/1995 |
| EP | 0647438 | 4/1995 |
| EP | 0658538 | 6/1995 |
| EP | 0662307 | 7/1995 |
| EP | 0669114 | 8/1995 |
| EP | 0679372 | 11/1995 |
| EP | 0684022 | 11/1995 |
| EP | 0686379 | 12/1995 |
| EP | 0688545 | 12/1995 |
| EP | 0709067 | 5/1996 |
| EP | 0709068 | 5/1996 |
| EP | 0734698 | 10/1996 |
| EP | 0790041 | 8/1997 |
| EP | 0792627 | 9/1997 |
| EP | 0796597 | 9/1997 |
| EP | 0800800 | 10/1997 |
| EP | 0801934 | 10/1997 |
| EP | 0806190 | 11/1997 |
| EP | 0821920 | 2/1998 |
| EP | 0824902 | 2/1998 |
| EP | 0827725 | 3/1998 |
| EP | 0870483 | 10/1998 |
| EP | 0873728 | 10/1998 |
| EP | 0 876 806 | 11/1998 |
| EP | 0876806 | 11/1998 |
| EP | 0 884 029 A1 | 12/1998 |
| EP | 0884029 | 12/1998 |
| EP | 0 890 346 A1 | 1/1999 |
| EP | 0890346 | 1/1999 |
| EP | 0897698 | 2/1999 |
| EP | 0910998 | 4/1999 |
| EP | 0928605 | 7/1999 |
| EP | 0 945 107 | 9/1999 |
| EP | 0938879 | 9/1999 |
| EP | 0943301 | 9/1999 |
| EP | 0945107 | 9/1999 |
| EP | 0947180 | 10/1999 |
| EP | 0948945 | 10/1999 |
| EP | 0956832 | 11/1999 |
| EP | 0968689 | 1/2000 |
| EP | 0970664 | 1/2000 |
| EP | 0983753 | 3/2000 |
| EP | 1008329 | 6/2000 |
| EP | 1025812 | 8/2000 |
| EP | 1093771 | 4/2001 |
| EP | 1245203 | 10/2002 |
| EP | 1356789 | 10/2003 |
| EP | 1378212 | 1/2004 |
| EP | 1437157 | 7/2004 |
| EP | 1123065 | 11/2006 |
| EP | 1852089 | 11/2007 |
| EP | 2204142 | 7/2010 |
| EP | 1341482 | 10/2010 |
| FR | 2758253 | 7/1998 |
| FR | 2764794 | 12/1998 |
| FR | 2774279 | 8/1999 |
| FR | 2785174 | 5/2000 |
| GB | 2281865 | 3/1995 |
| JP | 06-41745 | 6/1994 |
| JP | 9010318 | 1/1997 |
| JP | 9285549 | 11/1997 |
| JP | 10-165513 | 6/1998 |
| WO | WO 87/00442 | 1/1987 |
| WO | WO 90/09783 | 9/1990 |
| WO | WO 92/03107 | 3/1992 |
| WO | WO 93/06792 | 4/1993 |
| WO | WO 93/13825 | 7/1993 |
| WO | WO 94/17754 | 8/1994 |
| WO | WO 95/03010 | 2/1995 |
| WO | WO 95/09584 | 4/1995 |
| WO | WO 95/15108 | 6/1995 |
| WO | WO 95/18585 | 7/1995 |
| WO | WO 95/21592 | 8/1995 |
| WO | WO 95/26695 | 10/1995 |
| WO | WO 95/31945 | 11/1995 |
| WO | WO 95/32757 | 12/1995 |
| WO | WO 96/03092 | 2/1996 |
| WO | WO 96/09013 | 3/1996 |
| WO | WO 96/14028 | 5/1996 |
| WO | WO 96/25176 | 8/1996 |
| WO | WO 96/26689 | 9/1996 |
| WO | WO 96/28115 | 9/1996 |
| WO | WO 96/28116 | 9/1996 |
| WO | WO 96/34580 | 11/1996 |
| WO | WO 97/04721 | 2/1997 |

(56) References Cited

FOREIGN PATENT DOCUMENTS

| WO | WO 97/14375 | 4/1997 |
|---|---|---|
| WO | WO 97/16133 | 5/1997 |
| WO | WO 97/21399 | 6/1997 |
| WO | WO 97/25937 | 7/1997 |
| WO | WO 97/26840 | 7/1997 |
| WO | WO 97/32543 | 9/1997 |
| WO | WO 97/32544 | 9/1997 |
| WO | WO 97/33534 | 9/1997 |
| WO | WO 97/40780 | 11/1997 |
| WO | WO 97/40781 | 11/1997 |
| WO | WO 97/40782 | 11/1997 |
| WO | WO 97/40783 | 11/1997 |
| WO | WO 97/40874 | 11/1997 |
| WO | WO 97/45073 | 12/1997 |
| WO | WO 98/00090 | 1/1998 |
| WO | WO 98/20810 | 5/1998 |
| WO | WO 98/20927 | 5/1998 |
| WO | WO 98/26731 | 6/1998 |
| WO | WO 98/30173 | 7/1998 |
| WO | WO 98/32412 | 7/1998 |
| WO | WO 98/37833 | 9/1998 |
| WO | WO 98/40035 | 9/1998 |
| WO | WO 98/56312 | 12/1998 |
| WO | WO 99/01088 | 1/1999 |
| WO | WO 99/12495 | 3/1999 |
| WO | WO 99/15105 | 4/1999 |
| WO | WO 99/15107 | 4/1999 |
| WO | WO 99/17680 | 4/1999 |
| WO | WO 99/18888 | 4/1999 |
| WO | WO 99/38457 | 8/1999 |
| WO | WO 99/38458 | 8/1999 |
| WO | WO 99/39660 | 8/1999 |
| WO | WO 99/39661 | 8/1999 |
| WO | WO 99/40876 | 8/1999 |
| WO | WO 99/43272 | 9/1999 |
| WO | WO 99/44535 | 9/1999 |
| WO | WO 99/49810 | 10/1999 |
| WO | WO 99/49811 | 10/1999 |
| WO | WO 00/06051 | 2/2000 |
| WO | WO 00/13611 | 3/2000 |
| WO | WO 00/28921 | 5/2000 |
| WO | WO 00/28922 | 5/2000 |
| WO | WO 00/30563 | 6/2000 |
| WO | WO 00/42946 | 7/2000 |
| WO | WO 00/45742 | 8/2000 |
| WO | WO 00/69366 | 11/2000 |
| WO | WO 00/71053 | 11/2000 |
| WO | WO 01/01889 | 1/2001 |
| WO | WO 01/05331 | 1/2001 |
| WO | WO 01/26583 | 4/2001 |
| WO | WO 01/32099 | 5/2001 |
| WO | WO 01/32102 | 5/2001 |
| WO | WO 01/41675 | 6/2001 |
| WO | WO 01/58384 | 8/2001 |
| WO | WO 01/89421 | 11/2001 |
| WO | WO 02/22024 | 3/2002 |
| WO | WO 02/26281 | 4/2002 |
| WO | WO 02/055120 | 7/2002 |
| WO | WO 02/060344 | 8/2002 |
| WO | WO 02/078762 | 10/2002 |
| WO | WO 02/091958 | 11/2002 |
| WO | WO 03/017870 | 3/2003 |
| WO | WO 03/059207 | 7/2003 |
| WO | WO 03/082154 | 10/2003 |
| WO | WO 2004/087015 | 10/2004 |
| WO | WO 2007/053224 | 5/2007 |
| WO | WO 01/01885 | 1/2011 |

OTHER PUBLICATIONS

U.S. Appl. No. 08/396,565, Mar. 1, 1995, Brown, Brian J.
U.S. Appl. No. 60/076,946, Mar. 5, 1998, Tseng et al.
U.S. Appl. No. 60/254,688, Dec. 11, 2000, Addonizio.
U.S. Appl. No. 60/234,548, Sep. 22, 2000, Girton.
U.S. Appl. No. 60/238,178, Oct. 5, 2000, DiCaprio.
U.S. Appl. No. 60/272,651, Mar. 1, 2001, Doran.
U.S. Appl. No. 60/272,906, Mar. 1, 2001, Doran.
U.S. Appl. No. 08/396,569, Mar. 1, 1995, Brown.
U.S. Appl. No. 60/844,011, Sep. 12, 2006, Broome.
U.S. Appl. No. 60/859,460, Nov. 16, 2006, Yadin.
Preliminary Disclosure of the Claims Infringed by Orbusneich Medical Co. Ltd., BVI, Orbusneich Medical, Inc. (Sep. 30, 2011).
Preliminary Invalidity and Non-Infringement Contentions by Boston Scientific Corporation. (Nov. 30, 2011).
Brief by Boston Scientific Corporation *Boston Scientific Corporation's Opening Markman Brief.* (Jan. 5, 2012).
Preliminary Claim Construction Briefs by Orbusneich Medical Co. Ltd., BVI, Orbusneich Medical, Inc. (Jan. 5, 2012).
Freed et al., The Manual of Interventional Cardiology, 1992, Physician's Press, Birmingham, Michigan.
Freed et al., The New Manual of Interventional Cardiology, 1996, Physician's Press, Birmingham, Michigan.
Baim et al., Grossman's Cardiac Catheterization, Angiography, and Intervention, 2000, $6^{th}$ Edition, Lippincott Williams & Wilkins, Philadelphia, PA.
Schneider, P., Endovascular Skills, 1998, Quality Medical Publishing, Inc., St. Louis, MO.
Schatz, Richard A., et al., A View of Vascular Stents, Circulation, 1989; 79: 445-457.
Roguin et al., Acute and 30-Day Results of the Serpentine Balloon Expandable Stent Implantation in Simple and Complex Coronary Arterial Narrowings, Am. J. Cardiology, 1997; 80: 1155-1162, Excerpta Medica, Inc., Bridgewater, NJ.
Roguin et al., BeStent—The Serpentine Balloon Expandable Stent: Review of Mechanical Properties and Clinical Experience, Artif Organs, 1998; 22(3): 243-249, Blackwell Science, Inc., Malden, MA.
Brochure: AVE Micro Stent Instructions for Use, Applied Vascular Engineering, Inc.
Brochure: Gianturco-Rosch Biliary Z-Stents, 1989, Cook Incorporated, Bloomington, IN.
Roberson et al., Engineering Fluid Mechanics, $3^{rd}$ Edition, p. 94, pp. 414-421, Houghton Mifflin Company.
Carrasco et al., Expandable Biliary Endoprosthesis: An Experimental Study, American Journal of Roentgenology, 1985; 145: 1279-1281, American Roentgen Ray Society, Leesburg, VA.
Starck, E., First Clinical Experience with the Memotherm Vascular Stent, Stents—State of the Art and Future Developments, 1995: 59-62, Polyscience Publications, Inc., Morin Heights, Canada.
Irving et al., Gianturco Expandable Metallic Biliary Stents: Results of a European Clinical Trial, Interventional Radiology, 1989; 172 (2): 321-326, RSNA, Oak Brook, IL.
Levy, S.B., Improved Dilation Catheter Balloons, J. of Clinical Engineering, 1986; 2 (4): 291-296, Quest Publishing Co., Lippincott Williams & Wilkins, Phildelphia, PA.
Report: Japanese Infringement search on articulated expandable stents, Jul. 12, 1995.
Kalpakjian, S., Manufacturing Processes for Engineering Materials, p. 340, Addison-Wesley Publishing Company, Reading, MA.
Product Description, AVE Microstent, Applied Vascular Engineering, Inc.
Beyar et al., Newer Stents: Materials and Designs, J. Invas. Cardiol., 1997; 9(5): 363-371, HMP Communications LLC, Malvern, PA.
Melzer et al., Performance Improvement of Surgical Instrumentation Through the use of Nitinol Materials, The $1^{st}$ Int'l Conference on Shape Memory and Superelastic Technologies, 1994; 401-409, NDC, Fremont, CA.
Sigwart, U., The Self-Expanding Mesh Stent, Section IV, Chapter 29, 605-610.
Coons, H.G., Self-Expanding Stainless Steel Biliary Stents, Radiology, 1989; 170(3): 979-983, RSNA, Oak Brook, IL.
Information Packet for SMART Stent, Cordis Endovascular.
Uchida et al., Modifications of Gianturco Expandable Wire Stents, American Roentgen Ray Society, 1988; 150: 1185-1187, Leesburg, VA.
Jang, G.D., The Parallel-Serial Jang Stents, Handbook of Coronary Stents $2^{nd}$ Edition, 1998; pp. 229-234, Mosby, St. Louis, MO.
Beyar et al., The BeStent, Handbook of Coronary Stents $2^{nd}$ Edition, 1998; pp. 157-170, Mosby, St. Louis, MO.

(56) References Cited

OTHER PUBLICATIONS

Wallace et al., Tracheobronchial Tree: Expandable Metallic Stents Used in Experimental and Clinical Applications, Radiology, 1986; 158: 309-312, RSNA, Oak Brook, IL.
Cambridge Dictionary of Technology, p. 128, Cambridge University Press.
Photograph, Cordis MiniCrown Stent, presented at the Cardiovascular Summit (CVS), Dec. 9-13, 1997, Rotterdam, The Netherlands.
Photograph, Angiodynamics Angiostent, presented at the Cardiovascular Summit (CVS), Dec. 9-13, 1997, Rotterdam, The Netherlands.
Photograph, Biocompatibles Divysio stent (1996), presented at the Cardiovascular Summit (CVS), Dec. 9-13, 1997, Rotterdam, The Netherlands.
Photograph, Biocompatibles Divysio stent (views A and B, 1996), presented at the Cardiovascular Summit (CVS), Dec. 9-13, 1997, Rotterdam, The Netherlands.
Photograph, Uni-Cath Iris Stent (1996), presented at the Cardiovascular Summit (CVS), Dec. 9-13, 1997, Rotterdam, The Netherlands.
Photograph, Vascular Therapies Paragon Stent (1997), presented at the Cardiovascular Summit (CVS), Dec. 9-13, 1997, Rotterdam, The Netherlands.
Int'l Search Report for WO 03/071919 dated Nov. 3, 2003.
Photograph, Uni-Cath Spiral Force Stent (1997), presented at the Cardiovascular Summit (CVS), Dec. 9-13, 1997, Rotterdam, The Netherlands.
Photograph, Uni-Cath Iris II Stent (1997), presented at the Cardiovascular Summit (CVS), Dec. 9-13, 1997, Rotterdam, The Netherlands.
Photograph, Schneider Monorail Magic WallStent (1997), presented at the Cardiovascular Summit (CVS), Dec. 9-13, 1997, Rotterdam, The Netherlands.
Photograph, SciMed Radius Stent (1996), presented at the Cardiovascular Summit (CVS), Dec. 9-13, 1997, Rotterdam, The Netherlands.
Photograph, NIR NirSide Stent (1997), presented at the Cardiovascular Summit (CVS), Dec. 9-13, 1997, Rotterdam, The Netherlands.
Photograph, Schneider WallStent (1996), presented at the Cardiovascular Summit (CVS), Dec. 9-13, 1997, Rotterdam, The Netherlands.
Photograph, PAS Act-One Stent (1996), presented at the Cardiovascular Summit (CVS), Dec. 9-13, 1997, Rotterdam, The Netherlands.
Photograph, Occam Pro-Stent (1997), presented at the Cardiovascular Summit (CVS), Dec. 9-13, 1997, Rotterdam, The Netherlands.
Photograph, SciMed NIR Stent (1996), presented at the Cardiovascular Summit (CVS), Dec. 9-13, 1997, Rotterdam, The Netherlands.
Photograph, JOMED JO Stent Flex Coronary Stent (1997), presented at the Cardiovascular Summit (CVS), Dec. 9-13, 1997, Rotterdam, The Netherlands.
Photograph, NIR 5-Cell Stent (1997), presented at the Cardiovascular Summit (CVS), Dec. 9-13, 1997, Rotterdam, The Netherlands.
Photograph, NIR Conformer (1997), presented at the Cardiovascular Summit (CVS), Dec. 9-13, 1997, Rotterdam, The Netherlands.
Photograph, Navius Interventional Systems ZRI Stent (1997), presented at the Cardiovascular Summit (CVS), Dec. 9-13, 1997, Rotterdam, The Netherlands.
Photograph, Medtronic Wiktor I Stent (1996), presented at the Cardiovascular Summit (CVS), Dec. 9-13, 1997, Rotterdam, The Netherlands.
Photograph, Medtronic Hepamed Coated Coronary Stent (1997), presented at the Cardiovascular Summit (CVS), Dec. 9-13, 1997, Rotterdam, The Netherlands.
Photograph, Medtronic beStent (1996), presented at the Cardiovascular Summit (CVS), Dec. 9-13, 1997, Rotterdam, The Netherlands.
Photograph, JOMED JO Stent Plus Coronary Stent (1997), presented at the Cardiovascular Summit (CVS), Dec. 9-13, 1997, Rotterdam, The Netherlands.
Photograph, Medtronic beStent (1997), presented at the Cardiovascular Summit (CVS), Dec. 9-13, 1997, Rotterdam, The Netherlands.
Photograph, JOMED JO Stent S Side Branch (1997), presented at the Cardiovascular Summit (CVS), Dec. 9-13, 1997, Rotterdam, The Netherlands.
Photograph, JOMED JO Stent Graft Coronary Stent (1997), presented at the Cardiovascular Summit (CVS), Dec. 9-13, 1997, Rotterdam, The Netherlands.
Photograph, Cordis CrossFlex Stent (1996), presented at the Cardiovascular Summit (CVS), Dec. 9-13, 1997, Rotterdam, The Netherlands.
Photograph, PSJ-3 Stent (1997), presented at the Cardiovascular Summit (CVS), Dec. 9-13, 1997, Rotterdam, The Netherlands.
Photograph, Palmaz-Schatz Stent (1995), presented at the Cardiovascular Summit (CVS), Dec. 9-13, 1997, Rotterdam, The Netherlands.
Photograph, Iso Stent BX Stent (1996), presented at the Cardiovascular Summit (CVS), Dec. 9-13, 1997, Rotterdam, The Netherlands.
Photograph, JOMED JO Stent (1996), presented at the Cardiovascular Summit (CVS), Dec. 9-13, 1997, Rotterdam, The Netherlands.
Photograph, Cordis Coronary Stent, presented at the Cardiovascular Summit (CVS), Dec. 9-13, 1997, Rotterdam, The Netherlands.
Photograph, InStent CardioCoil Stent (1995), presented at the Cardiovascular Summit (CVS), Dec. 9-13, 1997, Rotterdam, The Netherlands.
Photograph, InFlow Dynamics InFlow Stent (1997), presented at the Cardiovascular Summit (CVS), Dec. 9-13, 1997, Rotterdam, The Netherlands.
Photograph, Global Therapeutics Freedom Force Stent (1995), presented at the Cardiovascular Summit (CVS), Dec. 9-13, 1997, Rotterdam, The Netherlands.
Photograph, Global Therapeutics V-Flex Stent (1997), presented at the Cardiovascular Summit (CVS), Dec. 9-13, 1997, Rotterdam, The Netherlands.
Photograph, Global Therapeutics V-Flex Plus Stent (1997), presented at the Cardiovascular Summit (CVS), Dec. 9-13, 1997, Rotterdam, The Netherlands.
Photograph, Bard X-trode Stent (1996), presented at the Cardiovascular Summit (CVS), Dec. 9-13, 1997, Rotterdam, The Netherlands.
Photograph, Devon Medical Pura Ostia Stent (1997), presented at the Cardiovascular Summit (CVS), Dec. 9-13, 1997, Rotterdam, The Netherlands.
Photograph, AVE GFX Stent (1996), presented at the Cardiovascular Summit (CVS), Dec. 9-13, 1997, Rotterdam, The Netherlands.
Photograph, Cordis Crown Stent, presented at the Cardiovascular Summit (CVS), Dec. 9-13, 1997, Rotterdam, The Netherlands.
Photograph, Devon Medical Pura Vario (1996), presented at the Cardiovascular Summit (CVS), Dec. 9-13, 1997, Rotterdam, The Netherlands.
Photograph, ACS Multilink Stent (1996), presented at the Cardiovascular Summit (CVS), Dec. 9-13, 1997, Rotterdam, The Netherlands.
Photograph, Cook Cardiology Gianturco-Roubin II Coronary Stent (1996), presented at the Cardiovascular Summit (CVS), Dec. 9-13, 1997, Rotterdam, The Netherlands.
Photograph, Biotronik Tenax Stent (1996), presented at the Cardiovascular Summit (CVS), Dec. 9-13, 1997, Rotterdam, The Netherlands.
Photograph, Biotronik Tensum 3 Stent (1996), presented at the Cardiovascular Summit (CVS), Dec. 9-13, 1997, Rotterdam, The Netherlands.
Photograph, ACS Act One Stent (1995), presented at the Cardiovascular Summit (CVS), Dec. 9-13, 1997, Rotterdam, The Netherlands.
Photograph, ACS Guidant Solo Stent (1997), presented at the Cardiovascular Summit (CVS), Dec. 9-13, 1997, Rotterdam, The Netherlands.
Photograph, AVE GFX (short) Stent, presented at the Cardiovascular Summit (CVS), Dec. 9-13, 1997, Rotterdam, The Netherlands.
Photograph, AVE Microstent II Stent, presented at the Cardiovascular Summit (CVS), Dec. 9-13, 1997, Rotterdam, The Netherlands.
Photograph, Devon Medical Pura Vario AS Stent, presented at the Cardiovascular Summit (CVS), Dec. 9-13, 1997, Rotterdam, The Netherlands.
Photograph, JOMED JO Stent B Bifurcation, presented at the Cardiovascular Summit (CVS), Dec. 9-13, 1997, Rotterdam, The Netherlands.

(56) References Cited

OTHER PUBLICATIONS

Photograph, Devon Medical PURA Side Arm Stent, presented at the Cardiovascular Summit (CVS), Dec. 9-13, 1997, Rotterdam, The Netherlands.
Photograph, Glastra Stent, presented at the Cardiovascular Summit (CVS), Dec. 9-13, 1997, Rotterdam, The Netherlands.
Photograph, Spectranetics R Stent, presented at the Cardiovascular Summit (CVS), Dec. 9-13, 1997, Rotterdam, The Netherlands.
Photograph, Palmaz-Schatz Crown Stent, presented at the Cardiovascular Summit (CVS), Dec. 9-13, 1997, Rotterdam, The Netherlands.
Photograph, Strecker Stent, presented at the Cardiovascular Summit (CVS), Dec. 9-13, 1997, Rotterdam, The Netherlands.
Photograph, Wiktor GX Stent, presented at the Cardiovascular Summit (CVS), Dec. 9-13, 1997, Rotterdam, The Netherlands.
Serruys et al., Handbook of Coronary Stents, First Edition, 1997; 41-49, Martin Dunitz Ltd., London, UK.
Serruys et al., Handbook of Coronary Stents, Second Edition, 1998, Martin Dunitz Ltd., London, UK.
U.S. District Court, District of Massachusetts (Boston), Civil Docket for Case No. 1:09-cv-10962-RGS (*Orbusneich Medical Co. Ltd., BVI et al.* v. *Boston Scientific Corporation*, filed Jun. 8, 2009).
Notice of Opposition in EP 1341482 dated Jul. 28, 2011.
Notice of Opposition in EP 1341482 dated Aug. 5, 2011.
Supplemental European Search Report for EP 02709424 dated Jul. 31, 2008.
Brief by Orbusneich Medical Co. Ltd., BVI, Orbusneich Medical, Inc. Opening Claim Construction Brief. (Jan. 10, 2011).
Brief by Boston Scientific Corporation *Boston Scientific Corporations Opening Markman Brief*. (Jan. 10, 2011).
Amended Complaint (Fourth) against Boston Scientific Corporation, filed by Orbusneich Medical Co. Ltd., BVI, Orbusneich Medical, Inc. (Aug. 31, 2011).
Answer to 151 Amended Complaint, Counterclaim against Orbusneich Medical Co. Ltd., BVI, Orbusneich Medical, Inc. by Boston Scientific Corporation. (Sep. 14, 2011).
Plaintiff's Responsive Claim Construction Brief filed by Orbusneich Medical Co. Ltd., BVI, Orbusneich Medical, Inc. (Feb. 3, 2012).
Brief by Boston Scientific Corporation *Defendant Boston Scientific Corporation's Responsive Markman Brief*. (Feb. 3, 2012).
Supplemental Declaration of Edward Han in Support of Boston Scientific Corporation's Responsive Claim Construction Brief (Feb. 3, 2012).
U.S. Appl. No. 95/001,902, Feb. 24, 2012, Addonizio et al.
U.S. Appl. No. 95/001,940, Mar. 22, 2012, Pazienza et al.
Decision on Request for Inter Partes Reexamination, dated May 8, 2012.
Office Action in U.S. Appl. No. 95/001,902, dated May 8, 2012.
Amendment in U.S. Appl. No. 12/178,915, dated Sep. 12, 2011.
Non-Final Office Action issued in U.S. Appl. No. 12/178,909 on Oct. 9, 2012.
Response to Office Action filed in U.S. Appl. No. 12/178,387 on Oct. 1, 2012.
Non-Final Office Action issued in U.S. Appl. No. 12/027,382 on Oct. 5, 2012.
Notice of Allowance issued in U.S. Appl. No. 12/178,915 on Oct. 1, 2012.
Response to Office Action filed in U.S. Appl. No. 12/727,567 on Sep. 27, 2012.
Amended 3rd Party Response filed in U.S. Reexamination Control No. 95/001,768 on Oct. 1, 2012.
Amended 3rd Party Response filed in U.S. Reexamination Control No. 95/001,769 on Oct. 1, 2012.
Amended 3rd Party Response filed in U.S. Reexamination Control No. 95/001,902 on Sep. 27, 2012.
Notification of Defective Paper filed in U.S. Reexamination Control No. 95/001,768 on Sep. 25, 2012.
Notification of Defective Paper filed in U.S. Reexamination Control No. 95/001,769 on Sep. 25, 2012.
Notification of Detective Paper filed in U.S. Reexamination Control No. 95/001,902 on Sep. 21, 2012.
IDS filed in U.S. Appl. No. 13/332,294 on Nov. 9, 2012.
IDS filed in U.S. Appl. No. 13/332,283 on Nov. 9, 2012.
IDS filed in U.S. Appl. No. 13/332,271 on Nov. 9, 2012.
IDS filed in U.S. Appl. No. 13/332,263 on Nov. 9, 2012.
IDS filed in U.S. Appl. No. 13/332,240 on Nov. 9, 2012.
IDS filed in U.S. Appl. No. 13/332,216 on Nov. 9, 2012.
IDS filed in U.S. Appl. No. 13/332,307 on Nov. 9, 2012.
IDS filed in U.S. Appl. No. 13/332,185 on Nov. 9, 2012.
IDS filed in U.S. Appl. No. 13/332,119 on Nov. 9, 2012.
IDS filed in U.S. Appl. No. 13/332,025 on Nov. 9, 2012.
IDS filed in U.S. Appl. No. 13/331,859 on Nov. 9, 2012.
Response to non-final Office Action filed in U.S. Appl. No. 13/301,268 on Oct. 18, 2012.
IDS filed in U.S. Appl. No. 13/301,268 on Nov. 9, 2012.
IDS filed in U.S. Appl. No. 13/295,744 on Nov. 9, 2012.
Response to non-final Office Action filed in U.S. Appl. No. 12/178,889 on Oct. 19, 2012.
Response to non-final Office Action filed in U.S. Appl. No. 12/178,906 on Oct 22, 2012.
Issue Notification in U.S. Appl. No. 12/178,915 dated Nov. 7, 2012.
Response to non-final Office Action filed in U.S. Appl. No. 12/178,895 on Nov. 8, 2012.
Response to non-final Office Action filed in U.S. Appl. No. 12/178,898 on Nov. 8, 2012.
RCE, Petition to Withdraw from Issue and Preliminary Amendment filed in U.S. Appl. No. 12/178,915 on Nov. 21, 2012.
Final Office Action in U.S. Appl. No. 12/178,906 mailed on Nov. 23, 2012.
Final Office Action in U.S. Appl. No. 12/178,387 mailed on Nov. 21, 2012.
Notice of Allowance in U.S. Appl. No. 12/727,567 mailed on Dec. 10, 2012.
Issue Fee Payment in U.S. Appl. No. 12/727,567 mailed on Dec. 12, 2012.
Response to final Office Action in U.S. Appl. No. 12/178,906 mailed on Dec. 5, 2012.
Final Office Action in U.S. Appl. No. 12/178,889 mailed on Dec. 6, 2012.
Response to non-final Office Action filed in U.S. Appl. No. 12/027,382 on Dec. 5, 2012.
Notice of Allowance in U.S. Appl. No. 12/178,915 mailed on Dec. 24, 2012.
Advisory Action in U.S. Appl. No. 12/178,906 mailed on Dec. 28, 2012.
Final Office Action in U.S. Appl. No. 12/178,898 mailed on Dec. 21, 2012.
Final Office Action and Interview Summary in U.S. Appl. No. 12/178,895.
Reexam Request as filed for Reexam Control No. 95/001,940 on Mar. 16, 2012.
Reexam Litigation Search for Reexam Control No. 95/001,940 dated Mar. 22, 2012.
Notice of Reexam Request Filing Date and Assignment for Reexam Control No. 95/001,940 mailed Mar. 27, 2012.
Power of Attorney in Reexam Control No. 95/001,940, Apr. 19, 2012.
Bibliographic Data Sheet for Reexam Control No. 95/001,940, Apr. 23, 2012.
Communication regarding Power of Attorney in Reexam Control No. 95/001,940, Apr. 24, 2012.
Reexam Order and non-final Action in Reexam Control No. 95/001,940, May 25, 2012.
Response after non-final Action—owner, timely filed with IDS in Reexam Control No. 95/001,940, Jul. 25, 2012.
Letter Acknowledging that in Improper Paper in a Reexam Proceeding has been returned/destroyed in Reexam Control No. 95/001,940, Sep. 25, 2012.
Third Party Requester Comments after non-final Action in Reexam Control No. 95/001,940, Oct. 1, 2012.
IDS in Reexam Control No. 95/001,940, Dec. 7, 2012.
Reexam Request with IDS, Reexam Control No. 95/001,929, Mar. 5, 2012.

(56) References Cited

OTHER PUBLICATIONS

Notice of Incomplete Ex Parte Reexam Request in Reexam Control No. 95/001,929, Mar. 16, 2012.
Reexam Certificate of Service in Reexam Control No. 95/001,929, Mar. 23, 2012.
Receipt of Corrected Original Inter Partes Request in Reexam Control No. 95/001,929, Mar. 23, 2012.
Title Report in Reexam Control No. 95/001,929, Mar. 27, 2012.
Notice of Reexam Request filing date Reexam Control No. 95/001,929, Mar. 27, 2012.
Notice of Assignment of Reexam Request in Reexam Control No. 95/001,929, Mar. 27, 2012.
Reexam Litigation Search in Reexam Control No. 95/001,929, Apr. 6, 2012.
Power of Attorney in Reexam Control No. 95/001,929, Apr. 19, 2012.
Bibliographic Data Sheet in Reexamination Control No. 95/001,929, Apr. 23, 2012.
Communication regarding Power of Attorney in Reexamination Control No. 95/001,929, Apr. 24, 2012.
Order Granting Reexam and Non-Final Action in Reexamination Control No. 95/001,929, May 25, 2012.
Response after Non-Final Action (Owner, timely, including IDS and Affidavits) in Reexamination Control No. 95/001,929, Jul. 25, 2012.
Third Party Requester Comments after Non-Final Action in Reexamination Control No. 95/001,929, Aug. 24, 2012.
Notification of Defective Paper in Reexam in Reexamination Control No. 95/001,929, Sep. 21, 2012.
Third Party Requester Comments after Non-Final Action in Reexamination Control No. 95/001,929, Sep. 26, 2012.
Information Disclosure Statement in Reexamination Control No. 95/001,929, Dec. 7, 2012.
U.S. Appl. No. 95/001,962, Feb. 24, 2012, Johnson et al.
Patent Owner's Response to Office Action filed Jul. 9, 2012 in U.S. Appl. No. 95/001,902.
Response to Office Action filed Jul. 5, 2012 in U.S. Appl. No. 12/178,387.
Non-final Office Action mailed Jul. 5, 2012 in U.S. Appl. No. 12/727,567.
Final Office Action mailed Jun. 29, 2012 in U.S. Appl. No. 12/178,915.
Request for Continued Examination with Track One Request filed Jun. 5, 2012 in U.S. Appl. No. 12/178,906.
Request for Continued Examination with Track One Request filed Jun. 5, 2012 in U.S. Appl. No. 12/178,915.
Advisory Action mailed Jun. 4, 2012 in U.S. Appl. No. 12/178,906.
Advisory Action mailed Jun. 4, 2012 in U.S. Appl. No. 12/178,915.
Response to Final Office Action filed May 22, 2012 in U.S. Appl. No. 12/178,915.
Third Party Requester Comments after Non-final Action filed Mar. 6, 2012 in Reexam Control No. 95/001,768.
Third Party Requester Comments after Non-final Action filed Mar. 6, 2012 in Reexam Control No. 95/001,769.
Final Office Action mailed Mar. 1, 2012 in U.S. Appl. No. 12/178,915.
PTO Communication granting Track One Request mailed Feb. 26, 2012 in U.S. Appl. No. 12/178,387.
Preliminary Amendment with Track One Request filed Feb. 13, 2012 in U.S. Appl. No. 12/178,387.
Patent Owner's Response to Office Action filed Feb. 6, 2012 in Reexam Control No. 95/001,768.
Patent Owner's Response to Office Action filed Feb. 6, 2012 in Reexam Control No. 95/001,769.
Response to Final Office Action filed Jan. 30, 2012 in U.S. Appl. No. 12/178,906.
Final Office Action mailed Jan. 10, 2012 in U.S. Appl. No. 12/178,906.
Non-final Office Action mailed Dec. 6, 2011 in Reexam Control No. 95/001,768.
Non-final Office Action mailed Dec. 6, 2011 in Reexam Control No. 95/001,769.
Applicant Initiated Interview Summary mailed Nov. 9, 2011 in U.S. Appl. No. 12/178,906.
Applicant Initiated Interview Summary mailed Sep. 9, 2011 in U.S. Appl. No. 12/178,387.
Advisory Action mailed Nov. 7, 2011 in U.S. Appl. No. 12/178,387.
Amendment with Terminal Disclaimer filed Nov. 7, 2011 in U.S. Appl. No. 12/178,906.
Right of Appeal Notice mailed Jul. 20, 2012 in Reexam Control No. 95/000,552.
Right of Appeal Notice mailed Jul. 20, 2012 in Reexam Control No. 95/000,542.
Non-final Office Action, issued Aug. 29, 2012 in U.S. Appl. No. 12/178,387.
Non-final Office Action, issued Aug. 29, 2012 in U.S. Appl. No. 12/178,906.
Non-final Office Action, issued Aug. 21, 2012 in U.S. Appl. No. 12/178,898.
Non-final Office Action, issued Aug. 20, 2012 in U.S. Appl. No. 12/178,895.
Third Party Comments, filed Aug. 8, 2012 in U.S. Reexam Control No. 95/001,902.
Non-Final Office Action, issued Aug. 13, 2012 in U.S. Appl. No. 12/178,889.
Amendment filed Aug. 2, 2012 in U.S. Appl. No. 12/178,915.
Interview Summary, issued on Jul. 26, 2012 in U.S. Appl. No. 12/178,915.
Dismissal of Reexamination Petition for Entering Color Drawings in U.S. Reexam Control No. 95/001,769, dated Jul. 20, 2012.
Pre-Appeal Brief Request for Review filed in U.S. Appl. No. 12/178,387, filed Apr. 22, 2013.
Final Office Action in U.S. Appl. No. 12/178,895 mailed Apr. 26, 2013.
Response to Feb. 5, 2013 Office Action in U.S. Appl. No. 12/027,382, filed Apr. 5, 2013.
Patent Owner Response in Reexamination Control No. 95/001,769 filed Apr. 4, 2013.
Response to Dec. 31, 2012 Office Action in U.S. Appl. No. 12/178,895, filed Apr. 1, 2013.
Patent Owner's Comments in Reexamination Control No. 95/001,768 filed Mar. 27, 2013.
Pre-Appeal Brief Request for Review in U.S. Appl. No. 12/178,889, filed Mar. 6, 2013.
Action Closing Prosecution (non-final) in Reexamination Control No. 95/001,769 mailed Mar. 4, 2013.
Request for Continued Examination in U.S. Appl. No. 12/178,906, filed Feb. 25, 2013.
Final Office Action in U.S. Appl. No. 12/178,909 mailed Mar. 1, 2013.
Action Closing Prosecution (non-final) in Reexamination Control No. 95/001,768 mailed Feb. 27, 2013.
Non-Final Office Action in U.S. Appl. No. 12/178,883 mailed Feb. 15, 2013.
Pre-Appeal Brief Request for Review in U.S. Appl. No. 12/178,898, filed Feb. 21, 2013.
Response in U.S. Appl. No. 12/178,909, filed Feb. 11, 2013.
Action Closing Prosecution (non-final) in Reexamination Control No. 95/001,902 mailed Feb. 21, 2013.
Final Office Action in U.S. Appl. No. 12/027,382 mailed on Feb. 5, 2013.
Advisory Action in U.S. Appl. No. 12/178,387 mailed Feb. 4, 2013.
Response in U.S. Appl. No. 12/178,387, filed Jan. 22, 2013.
Amendment After Final in U.S. Appl. No. 13/295,744, filed Jan. 24, 2013.
Advisory Action in U.S. Appl. No. 13/295,744 mailed Feb. 13, 2013.
Notice of Appeal Filed in U.S. Appl. No. 13/295,744, filed Apr. 5, 2013.
Fax to Examiner of Interview Agenda, U.S. Appl. No. 13/295,744 dated Jan. 4, 2013.
Interview Summary in U.S. Appl. No. 13/295,744 dated Jan. 11, 2013.
Response in U.S. Appl. No. 13/332,025, filed Jan. 18, 2013.
Response in U.S. Appl. No. 13/332,307, filed Feb. 28, 2013.

(56) References Cited

OTHER PUBLICATIONS

Interview Summary in U.S. Appl. No. 13/332,307 mailed Apr. 25, 2013.
Response in U.S. Appl. No. 13/332,263, filed Feb. 28, 2013.
Interview Summary in U.S. Appl. No. 13/332,263 mailed Apr. 26, 2013.
Response in U.S. Appl. No. 13/332,283, filed Feb. 28, 2013.
Interview Summary in U.S. Appl. No. 13/332,283 mailed Apr. 25, 2013.

* cited by examiner

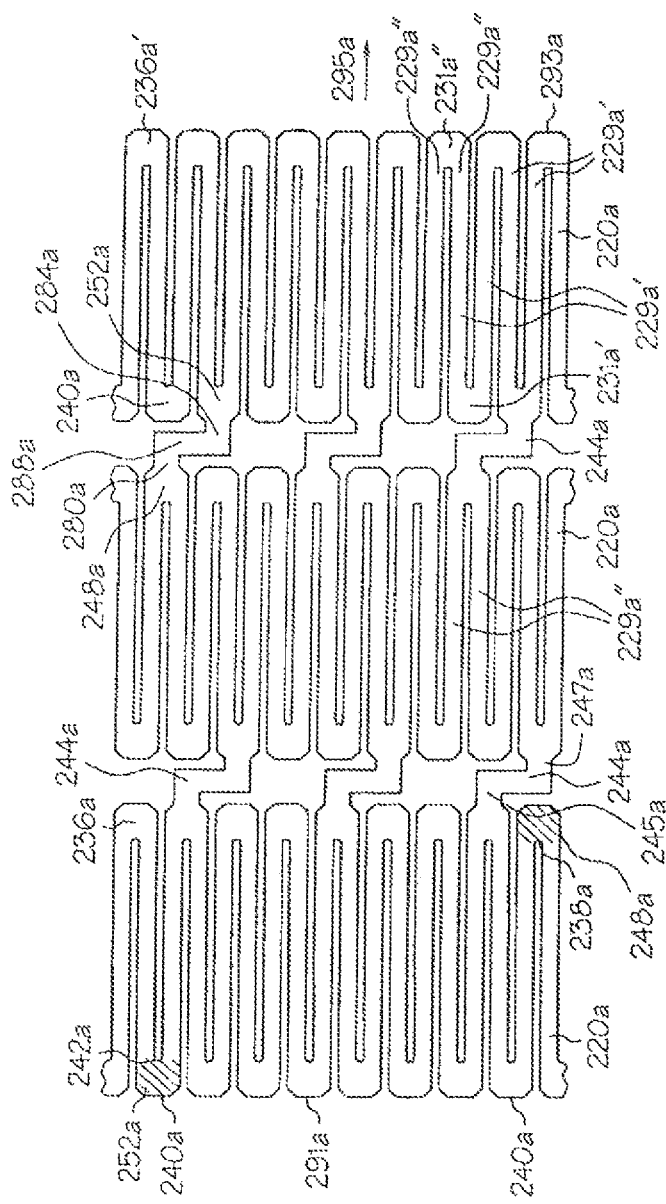

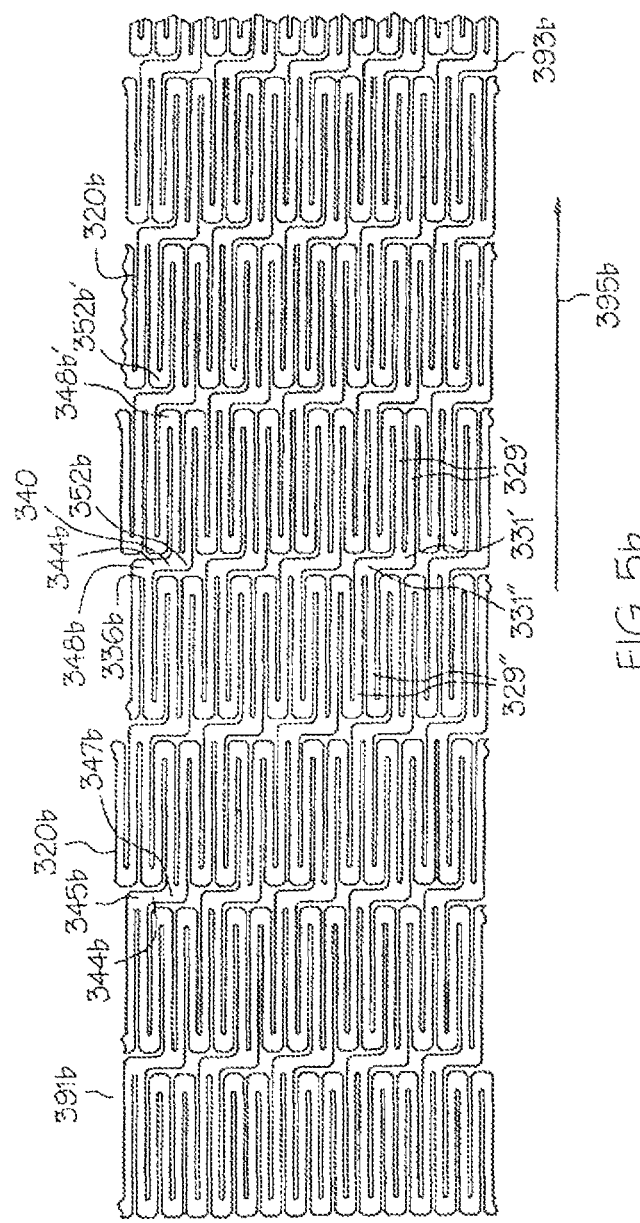

LONGITUDINALLY FLEXIBLE EXPANDABLE STENT

CROSS-REFERENCE TO RELATED APPLICATIONS

This Application is a Continuation Application of U.S. application Ser. No. 13/195,581, filed Aug. 1, 2011, which is a Continuation Application of U.S. application Ser. No. 10/705,273, now U.S. Pat. No. 7,988,717, filed Nov. 10, 2003, which is a Continuation Application of U.S. application Ser. No. 09/197,278, now U.S. Pat. No. 7,204,848, filed Nov. 20, 1998, which is a Continuation-in-Part of U.S. application Ser. No. 08/511,076, now U.S. Pat. No. 6,818,014, filed Aug. 3, 1995, which is a Continuation-in-Part Application of U.S. application Ser. No. 08/396,569, filed Mar. 1, 1995 and now abandoned, and the disclosure of all are hereby incorporated by reference.

Further, this application is a Continuation of Ser. No. 10/800,572, filed Mar. 15, 2004, which is Continuation of Ser. No. 09/197,278, filed Nov. 20, 1998, and issued as U.S. Pat. No. 7,204,848 on Apr. 17, 2004, which is a Continuation-in-Part of application Ser. No. 08/511,076, filed Aug. 3, 1995, and issued as U.S. Pat. No. 6,818,014 on Nov. 16, 2004, which is a Continuation-in-Part of application Ser. No. 08/396,569, abandoned, filed Mar. 1, 1995, the disclosures of which are hereby incorporated by reference.

FIELD OF THE INVENTION

This invention relates to an endoprosthesis device for implantation within a body vessel, typically a blood vessel. More specifically, it relates to a tubular expandable stent of improved longitudinal flexibility.

BACKGROUND OF THE INVENTION

Stents are placed or implanted within a blood vessel for treating stenoses, strictures or aneurysms therein. They are implanted to reinforce collapsing, partially occluded, weakened, or dilated sections of a blood vessel. They have also been implanted in the urinary tract and in bile ducts.

Typically, a stent will have an unexpanded (closed) diameter for placement and an expanded (opened) diameter after placement in the vessel or the duct. Some stents are self-expanding and some are expanded mechanically with radial outward force from within the stent, as by inflation of a balloon.

An example of the latter type is shown in U.S. Pat. No. 4,733,665 to Palmaz, which issued Mar. 29, 1988, and discloses a number of stent configurations for implantation with the aid of a catheter. The catheter includes an arrangement wherein a balloon inside the stent is inflated to expand the stent by plastically deforming it, after positioning it within a blood vessel.

A type of self-expanding stent is described in U.S. Pat. No. 4,503,569 to Dotter which issued Mar. 12, 1985, and discloses a shape memory stent which expands to an implanted configuration with a change in temperature. Other types of self-expanding stents not made of shape memory material are also known.

This invention is directed to stents of all these types when configured so as to be longitudinally flexible as described in detail hereinbelow. Flexibility is a desirable feature in a stent so as to conform to bends in a vessel. Such stents are known in the prior art. Examples are shown in U.S. Pat. No. 4,856,516 to Hillstead; U.S. Pat. No. 5,104,404 to Wolff; U.S. Pat. No. 4,994,071 to MacGregor; U.S. Pat. No. 5,102,417 to Palmaz; U.S. Pat. No. 5,195,984 to Schatz; U.S. Pat. No. 5,135,536 to Hillstead; U.S. Pat. 5,354,309 to Shepp-Pesch et al.; EPO Patent Application 0 540 290 A2 to Lau; EPO Patent Application No. 0 364 787 B1 to Schatz, and PCT Application WO 94/17754 (also identified as German Patent Application 43 03 181).

Generally speaking, these kinds of stents are articulated and are usually formed of a plurality of aligned, expandable, relatively inflexible, circular segments which are interconnected by flexible elements to form a generally tubular body which is capable of a degree of articulation or bending. Unfortunately, a problem with such stents is that binding, overlapping or interference can occur between adjacent segments on the inside of a bend due to the segments moving toward each other and into contact or on the outside of a bend the segments can move away from each other, leaving large gaps. This can lead to improper vessel support, vessel trauma, flow disturbance, kinking, balloon burst during expansion, and difficult recross for devices to be installed through already implanted devices and to unsupported regions of vessel.

A diamond configuration with diagonal connections between each and every diamond of each segment is also known but such closed configurations lack flexibility.

It is an object of this invention to provide a longitudinally flexible stent of open configuration that avoids these problems and exhibits improved flexibility (radially and longitudinally) in the stent body segments thereof rather than in flexible joints between the segments.

It is a further object of the present invention to provide a stent that is flexible yet also allows for side branch access.

SUMMARY OF THE INVENTION

It is a goal of the present invention to provide a flexible stent formed of interconnected bands which provides for side branch access and which further avoids the problem of pinching or overlap between adjacent bands. Pinching or overlap is avoided where peaks and troughs of adjacent bands are circumferentially displaced relative to each other. The stents of the present invention accomplish this goal by having different bands characterized by different wavelengths over the length of the stent and/or disposing the interconnecting members in such a way that after expansion of the stent, the phase relationship between adjacent bands is altered with the peaks and troughs displaced circumferentially relative to each other.

The inventive expandable stents are formed of a plurality of interconnected band-like elements characterized by alternating peaks and troughs. The ends of the interconnecting members which join adjacent bands are circumferentially offset and optionally, longitudinally offset. Peaks and troughs in adjacent bands are circumferentially offset as well so that the stent, in an expanded state, will have minimal overlap of peaks and troughs.

To this end, the invention provides a tubular, flexible, expandable stent, comprising a plurality of undulating band-like elements of a selected wavelength or wavelengths. The band-like elements have peaks and troughs and are aligned on a common longitudinal axis to define a generally tubular stent body. The peaks and troughs take a generally longitudinal direction along the stent body. Adjacent band-like elements may be in phase or out of phase with each other. The inventive stents further comprise a plurality of interconnecting elements having first ends and second ends. The first and second ends extend from adjacent band-like elements and are displaced from one another in a longitudinal direction and in a radial direction along the stent. Desirably, upon expansion of the stent, at least some of the peaks and troughs of a given band-like element are displaced relative to each other about the periphery of the stent to accommodate longitudinal flexing of the stent within the band-like elements and without interference between adjacent band-like elements.

In one embodiment, two different types of band-like elements are present in the stent, first band-like elements with a first selected wavelength and second band-like elements with a second selected wavelength exceeding the first selected wavelength. The first and second band-like elements preferably alternate over the length of the stent. Although the terminology of 'first band-like element' and 'second band-like element' is used, it is not intended to convey the relative order of appearance of the elements in the inventive stents.

In another embodiment, two different types of band-like elements are present, first and second band-like elements, each of which has peaks and troughs. The first band-like elements have more peaks (or troughs) than the second band-like elements. Similarly, the invention is also directed to embodiments having first and second band-like elements with peaks and troughs where the peaks (or troughs) of the first band-like elements are spaced closer together than the peaks (or troughs) of the second band-like elements.

In another embodiment in which band-like elements of only one wavelength are present, adjacent bands are about 180 E out of phase with one another. Interconnecting elements extend at an oblique angle relative to the longitudinal axis from a peak to a trough on an adjacent band.

In another embodiment in which band-like elements of only one wavelength are present, peaks from which interconnecting elements emanate are elongated relative to the peaks which are not connected to troughs and similarly, the troughs from which interconnectors emanate are elongated relative to troughs which are not connected to peaks. Further, each interconnecting element extends from the side of a peak to the side of a trough on an adjacent band.

In yet another embodiment in which band-like elements of only one wavelength are present, adjacent bands are about 90 E out of phase with one another. Each interconnecting element extends between a peak and a trough and the ends of the interconnecting member are circumferentially offset from one another and, optionally, longitudinally offset.

The invention further provides a tubular, flexible, expandable stent having a longitudinal axis, comprising one or more cylindrical shaped first segments having first struts, the first segment being defined by a member formed in an undulating pattern of interconnected paired first struts and in which adjacent pairs of first struts in a given first segment are interconnected at opposite ends and one or more cylindrical shaped second segments defined by a member formed in an undulating pattern of interconnected paired second struts and in which adjacent pairs of second struts in a given second segment are interconnected at opposite ends. The first struts are shorter than the second struts. The first segments are formed of a number of first struts and the second segments are formed of a number of second struts with the number of first struts in a first segment exceeding the number of second struts in a second segment. The first and second segments, present and desirably alternating along the stent body, are aligned on a common longitudinal axis to define a generally tubular stent body. Adjacent first and second segments are connected by a plurality of interconnecting elements, each interconnecting element extending from an end of paired first struts on a first segment to an end of paired second struts on an adjacent second segment. The ends of interconnecting elements are circumferentially offset relative to each other, and optionally, longitudinally offset. Desirably, upon expansion of the stent, the paired struts of the adjacent segments are displaced relative to each other about the periphery of the stent body to accommodate longitudinal flexing of the stent within the segments and without interference between adjacent segments.

BRIEF DESCRIPTION OF THE FIGURES

FIG. 4a shows a flat view of a stent configuration according to the invention.

FIG. 5b shows a flat view of a stent configuration according to the invention.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

Figure 1A:
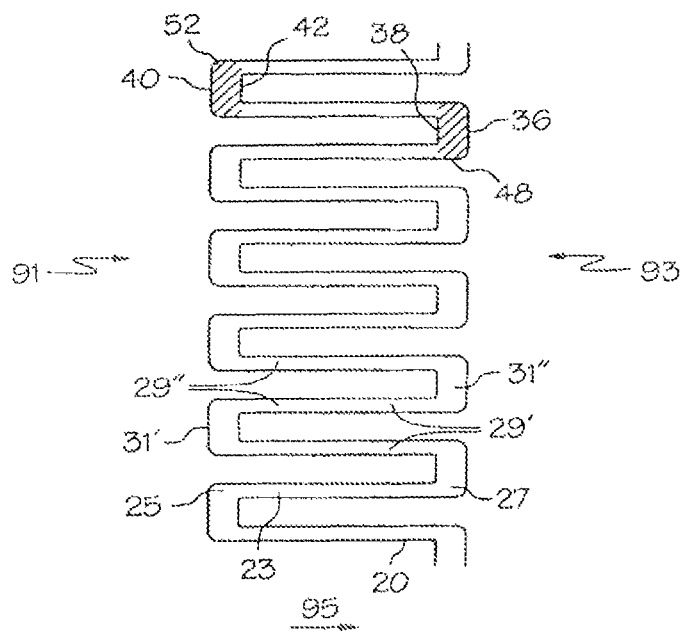
FIG. 1a shows a band-like element used in the inventive stents.
Figure 1B:
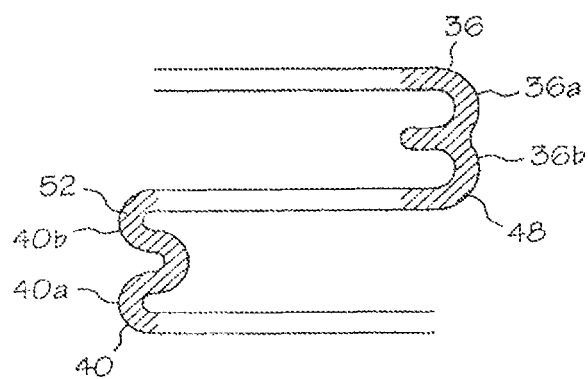
FIG. 1b shows a schematic of a peak region which contains a double peak and a trough region containing a double trough.

For the sake of consistency, the terms 'peak' and 'trough' shall be defined with respect to the proximal and distal ends of the stent. Each of the stents has a proximal end 91 and a distal end 93 and a longitudinal axis 95, as seen in FIG. 1a. Peaks 36 are generally concave relative to the proximal end of the stent and generally convex relative to the distal end of the stent. Troughs 40, on the other hand, are generally convex relative to the proximal end of the stent and generally concave relative to the distal end of the stent. Notwithstanding this definition, the term peak is also intended to extend to regions 48 that are generally peak-like which may, nevertheless, contain trough-like regions within the peak-like region as seen in FIG. 1b. Similarly the term trough is also intended to extend to regions 52 that are generally trough-like which may, nevertheless, contain peak-like regions within the trough-like region as seen in FIG. 1b.

Corresponding to each peak 36 is an inner diameter peak 38 where the inner diameter of the band-like element reaches its peak. The set of points on a given band-like element which are distal to inner diameter peak 38 is denoted peak region 48. Similarly, corresponding to each trough 40 is an inner diameter trough 42 where the inner diameter of the band-like element reaches its trough. The set of points on a given band-like element which are proximal to inner diameter trough 42 is denoted trough region 52. For the sake of clarity, unless otherwise indicated, analogous portions of stents will be similarly labeled, using three digit reference numerals to distinguish among the various embodiments shown.

Also included within this definition of peak regions and trough regions are peak regions which are comprised of multiple peaks as well as trough regions which are comprised of multiple troughs such as those shown schematically in FIG. 1b. Peak 36 is seen to consist of two sub-peaks 36a,b and trough 40 is similarly seen to consist of two sub-troughs 40a,b. In the case of peaks containing sub-peak and troughs containing sub-troughs, the peak region 48 includes all of the points along the band-like element between the sub-peaks that make up the peak and similarly, the trough region 52 includes all of the points along the band-like element between the sub-troughs that make up the trough.

The inventive stents may incorporate one or more bands of a chosen wavelength. In some embodiments, the inventive stents include one or more small amplitude, short wavelength bands to provide for flexibility and one or more large amplitude, long wavelength bands to give side branch access or to provide for sections of alternative strengths such as soft and/or stiff sections.

Figure 2:
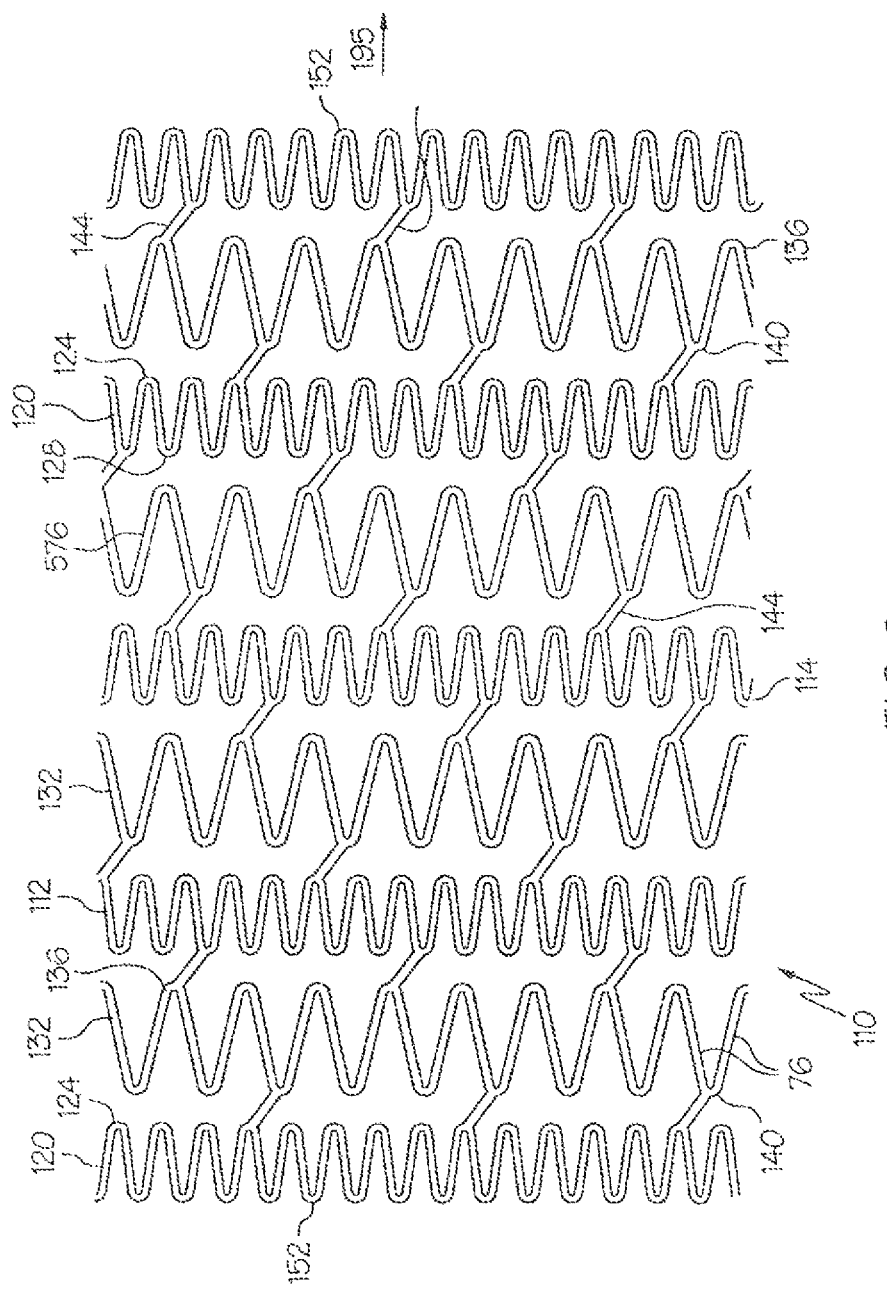
FIG. 2 shows a flat view of a stent configuration according to the invention.
Figure 3:
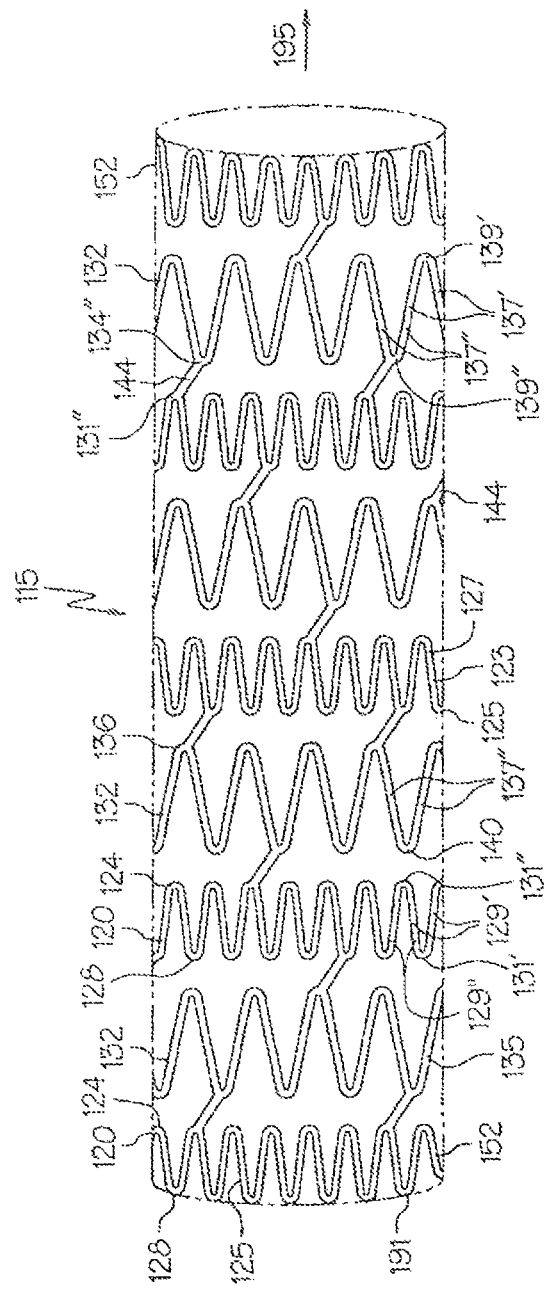
FIG. 3 shows the pattern of FIG. 2 in a tubular stent.

Turning to the Figures, FIG. 2 shows a flat view of a stent configuration and FIG. 3 shows the stent of FIG. 2 in tubular form. That is, the stent is shown for clarity in FIG. 2 in the flat and may be made from a flat pattern 110 (FIG. 2) which is formed into a tubular shape by rolling the pattern so as to bring edges 112 and 114 together (FIG. 2). The edges may then joined as by welding or the like to provide a cylindrical configuration such as that shown generally at 115 in FIG. 3.

A more preferred method of manufacture begins with a thin walled tube which is then laser cut to provide the desired configuration. It may also be chemically etched or EDM'd (electrical discharge machined) to form an appropriate configuration.

The configuration can be seen in these Figures to be made up of one or more spaced first band-like elements 120. First band-like elements have a generally serpentine configuration to provide continuous waves to the first band-like elements. The waves are characterized by a plurality of peaks 124 and troughs 128 taking a generally longitudinal direction along the cylinder such that the waves in first band-like elements 120 open as the stent is expanded from an unexpanded state having a first diameter to an expanded state having a second diameter.

The stent further comprises a plurality of spaced second band-like elements 132 having a generally serpentine configuration to provide continuous waves to the second band-like elements. The waves are characterized by a plurality of peaks 136 and troughs 140 taking a generally longitudinal direction along the cylinder such that the waves in the second band-like elements open as the stent is expanded from an unexpanded state having a first diameter to an expanded state having a second diameter. First and second band-like elements are characterized by respective wavelengths and amplitudes with the wavelength and amplitude of the second band-like elements exceeding the wavelength and amplitude of the first band-like elements.

Adjacent first band-like elements 120 and second band-like elements 132 are interconnected via a plurality of interconnecting elements 144. The ends of interconnecting element are circumferentially offset from each other.

In an embodiment, as shown in FIGS. 2 and 3, first band-like elements 120 and second band-like elements 132 alternate over the length of the stent. Optionally, as shown in FIGS. 2 and 3, each end 152 of the stent may terminate in a first band-like element. The invention also, however, contemplates each end terminating in a second band-like element, or further, one end terminating in a first band-like element and the other end terminating in a second band-like element.

While a minimum of one connecting element is required to join adjacent band-like elements, two or more interconnecting elements are preferred. In one embodiment, as shown in FIGS. 2 and 3, adjacent first and second band-like elements 120 and 132 are connected with three interconnecting elements 144. Further, in one embodiment, adjacent interconnecting elements 144 extending from peaks 136 on a first band-like element 120 are spaced five peaks apart on the first band-like element while adjacent interconnecting elements 144 extending from troughs 140 on a second band-like element 132 are spaced three troughs apart on the second band-like element. It is a further feature of the present invention that peaks 124 on first band-like elements 120 are circumferentially displaced on the periphery of the stent from troughs 140 on adjacent second band-like elements 132. It is desirable that peaks and troughs be displaced in the expanded state of the stent to minimize the possibility of pinching or overlap between adjacent band-like elements.

Although the stent of FIG. 2 is comprised of two different wavelength band-like elements, the invention contemplates stents with a plurality of different wavelength band-like elements. As such, other stents may have three, four or more different wavelength band-like elements.

Figure 4B:
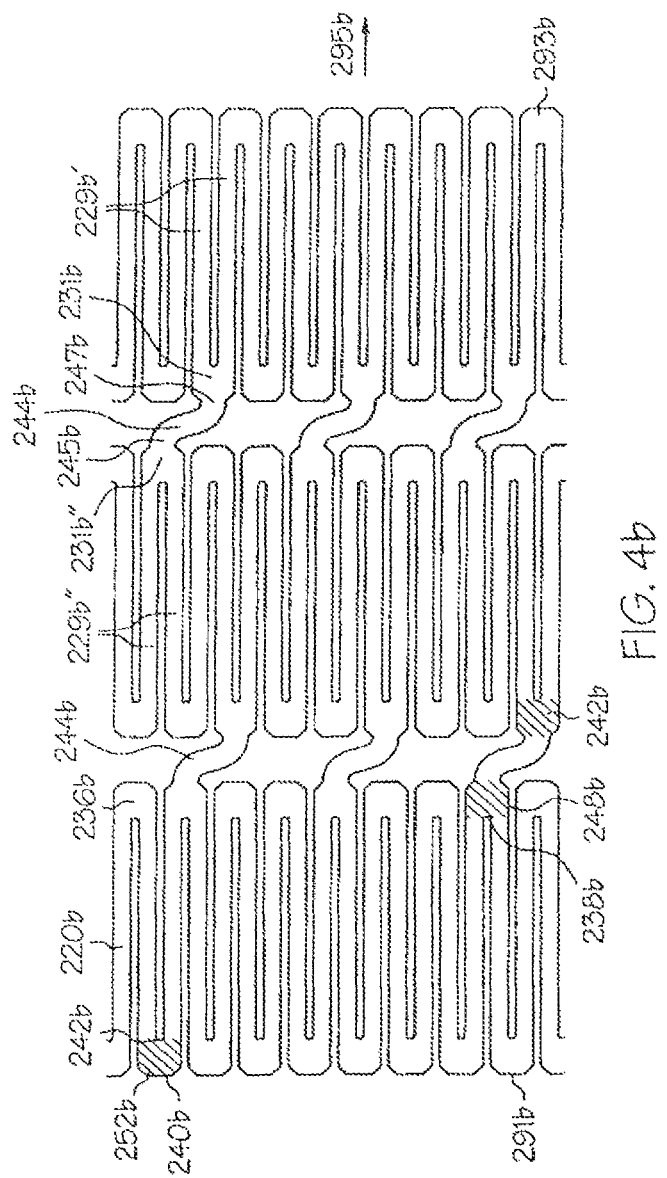
FIG. 4b shows a flat view of a stent configuration according to the invention.

In another embodiment, the inventive stent is comprised of band-like elements of a single wavelength, interconnected by interconnecting elements. Turning to FIGS. 4a and 4b, band-like elements 220a,b are interconnected by interconnecting elements 244a,b. Adjacent band-like elements 220a,b are 180E out of phase with one another. In the compressed state, the band-like elements consist of a plurality of peaks 236a,b and troughs 240a,b. Peak region 248a,b and trough region 252a,b have been shaded in one instance for illustrative purposes.

In the embodiment shown in FIG. 4a, each interconnecting element 244a extends between a peak region 248a and a trough region 252a. Rectilinear interconnecting elements 244a consist of a first shank 280a, a second shank 284a and a link 288a disposed in-between the first and second shanks 280a and 284a. First shank 280a extends in a longitudinal direction from peak region 248a and is substantially perpendicular to link 288a. Second shank 284a extends in a longitudinal direction from trough region 252a and is perpendicular to link 288a.

In the embodiment shown in FIG. 4b, the stent differs from the embodiment of FIG. 4a in that interconnecting element 244b extending between a peak region 248b and a trough region 252b is curvilinear rather than rectilinear.

In both FIGS. 4a and 4b, the interconnecting elements are seen to emanate from the middle of the peak and trough regions.

Figure 5A:
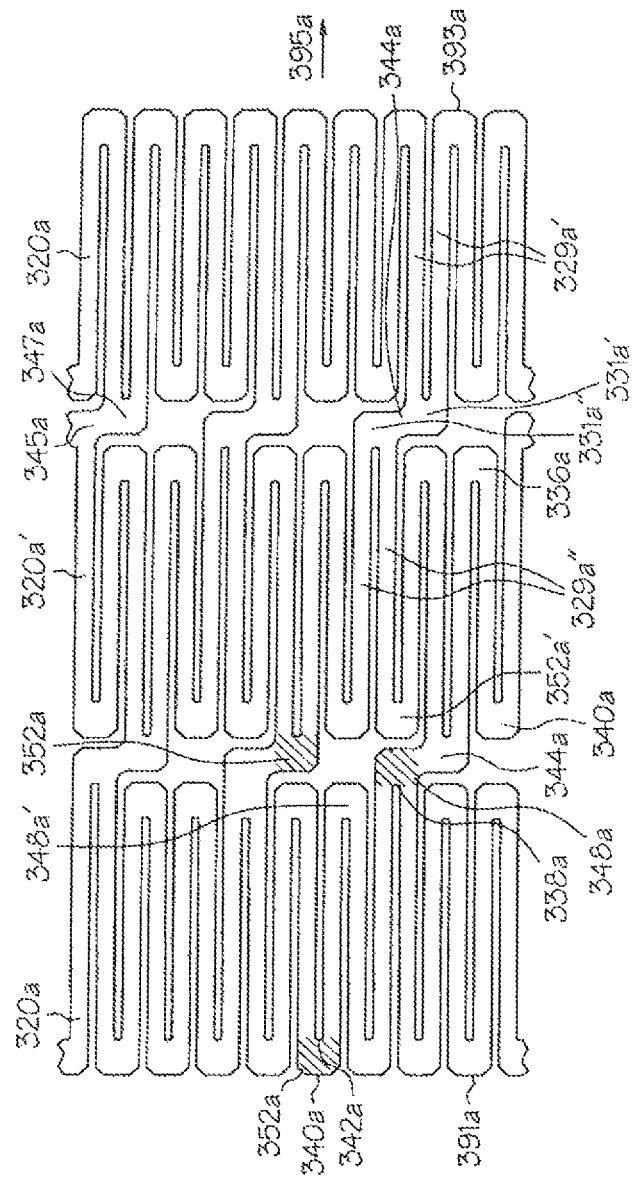
FIG. 5a shows a flat view of a stent configuration according to the invention.

In another embodiment, as shown in FIG. 5a, the inventive stent is comprised of band-like elements 320a of a single wavelength, interconnected by interconnecting elements 344a. Adjacent band-like elements 320a are 180E out of phase with one another. The band-like elements consist of a plurality of peaks 336a and troughs 340a. Interconnecting elements 344a extend between a peak region 348a and a trough region 352a. The peak regions 348a and trough regions 352a from which interconnecting elements 344a emanate on a given band-like element 320a are seen to extend longitudinally beyond adjacent peak regions 348a' and trough regions 352a' from which no interconnecting elements extend. The extension is such that at least a portion of peak regions 348a overlap longitudinally along the stent with at least a portion of trough region 352a on an adjacent band-like element 320a'. Of course, the overlap is limited to the longitudinal direction and not to the circumferential direction.

In another embodiment, as shown in FIG. 5b, interconnecting elements 344b extend between peak region 348b and a second closest trough region 352b on an adjacent band-like element. Interconnecting elements 344b are seen to be perpendicular to the longitudinal axis. As in the stent of FIG. 5a, peak regions 348b from which interconnecting elements 344b extend and trough regions 352b from which interconnecting elements 344b extend may extend beyond adjacent peak regions 348b' and trough regions 352b' from which no interconnecting elements 344b emanates.

Figure 6:
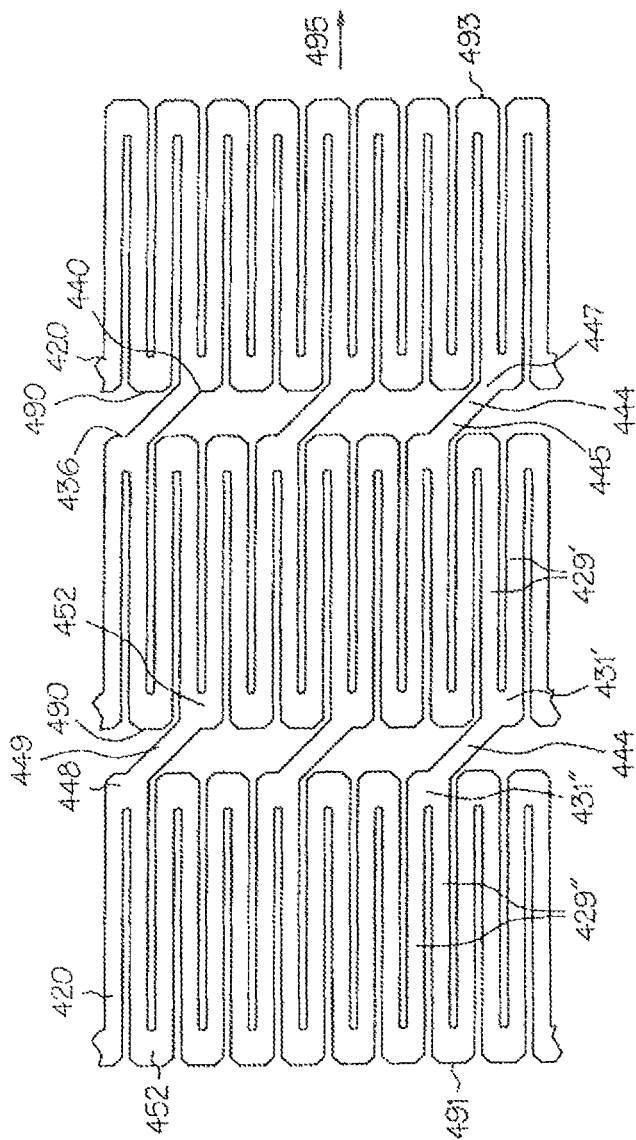
FIG. 6 shows a flat view of a stent configuration according to the invention.

In another embodiment, as shown in FIG. 6, adjacent band-like elements 420 are in phase with each other. As in previous Figs, band-like elements 420 are of a single wavelength, interconnected by interconnecting elements 444. The band-like elements consist of a plurality of peaks 436 and troughs 440. Interconnecting elements 444 extend at an oblique angle relative to the longitudinal axis of the stent between a peak region 448 and a trough region 452. As such, ends of interconnecting elements 444 are circumferentially offset relative to each other. The exact angle will, of course, depend on the region from which the interconnecting elements extend, as well as on whether interconnecting elements interconnect nearest peaks and troughs, next nearest peaks and troughs or peaks and troughs that are further separated.

In FIGS. 5a, 5b and 6, the interconnecting elements are seen to emanate from the sides of the peak and trough regions.

Figure 7:
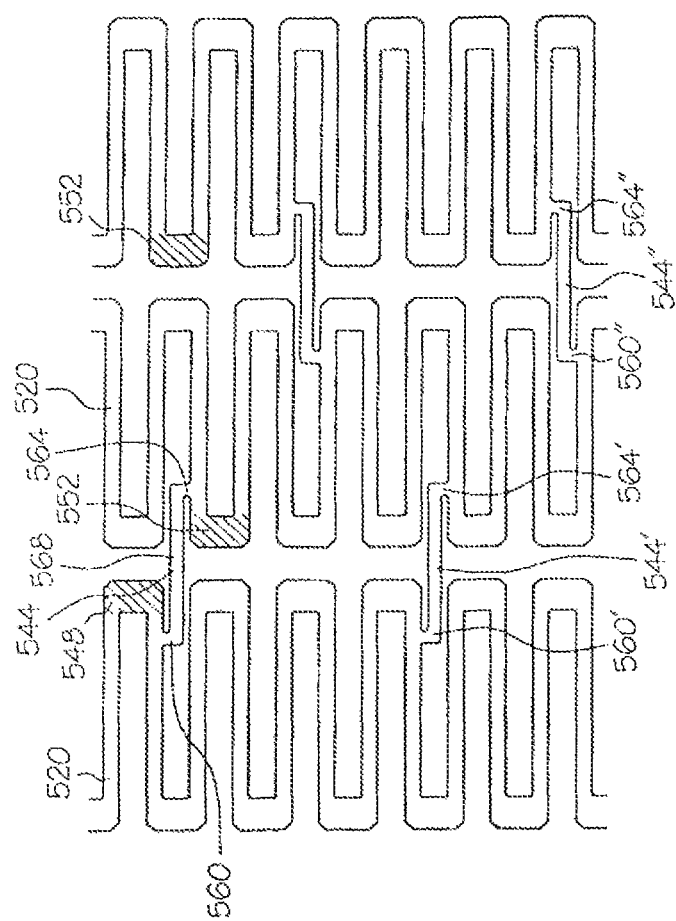
FIG. 7 shows a flat view of a stent configuration according to the invention.

Although for the embodiments of FIGS. 1-6, the interconnecting elements extend from peak regions on band-like elements to trough regions on adjacent band-like elements, the invention further contemplates interconnecting elements extending from a position between a peak region and an adjacent trough region on a band-like element to a position intermediate a trough region and a peak region on an adjacent second band-like element as in FIG. 7.

In the embodiment of FIG. 7, interconnecting elements are seen to extend from a region between the peak region and the trough region on a band-like element. The stent is formed of adjacent band-like elements 520 which are 180E degrees out of phase with one another. Interconnecting elements 544 extend from a region intermediate a peak region 548 and a trough region 552 on a band-like element to a region intermediate a peak region 548 and a trough region 552 on an adjacent band-like element. Interconnecting elements 544 consist of a first shank 560, a second shank 564, and an intermediate member 568 disposed in-between first and second shanks 560 and 564. First shank 560 and second shank 564 are substantially perpendicular to intermediate member 568 which extends in the longitudinal direction. Although not depicted, the region from which interconnecting elements 544 emanate may be midway between peaks and troughs.

The embodiment of FIG. 7 also differs from the embodiments of FIGS. 2-6 in the orientation of the interconnecting elements. Whereas the interconnecting elements in FIGS. 2-6 are all similarly oriented, in the embodiment of FIG. 7, the orientation of interconnecting elements alternates between adjacent pairs of adjacent band-like elements. Specifically, second shanks 564' of interconnecting elements 544' are seen to be displaced in a clockwise circumferential direction along the stent relative to first shanks 560', and seconds shank 564" of interconnecting elements 544" are seen to be displaced in a counterclockwise circumferential direction along the stent relative to while first shank 560".

Figure 8:
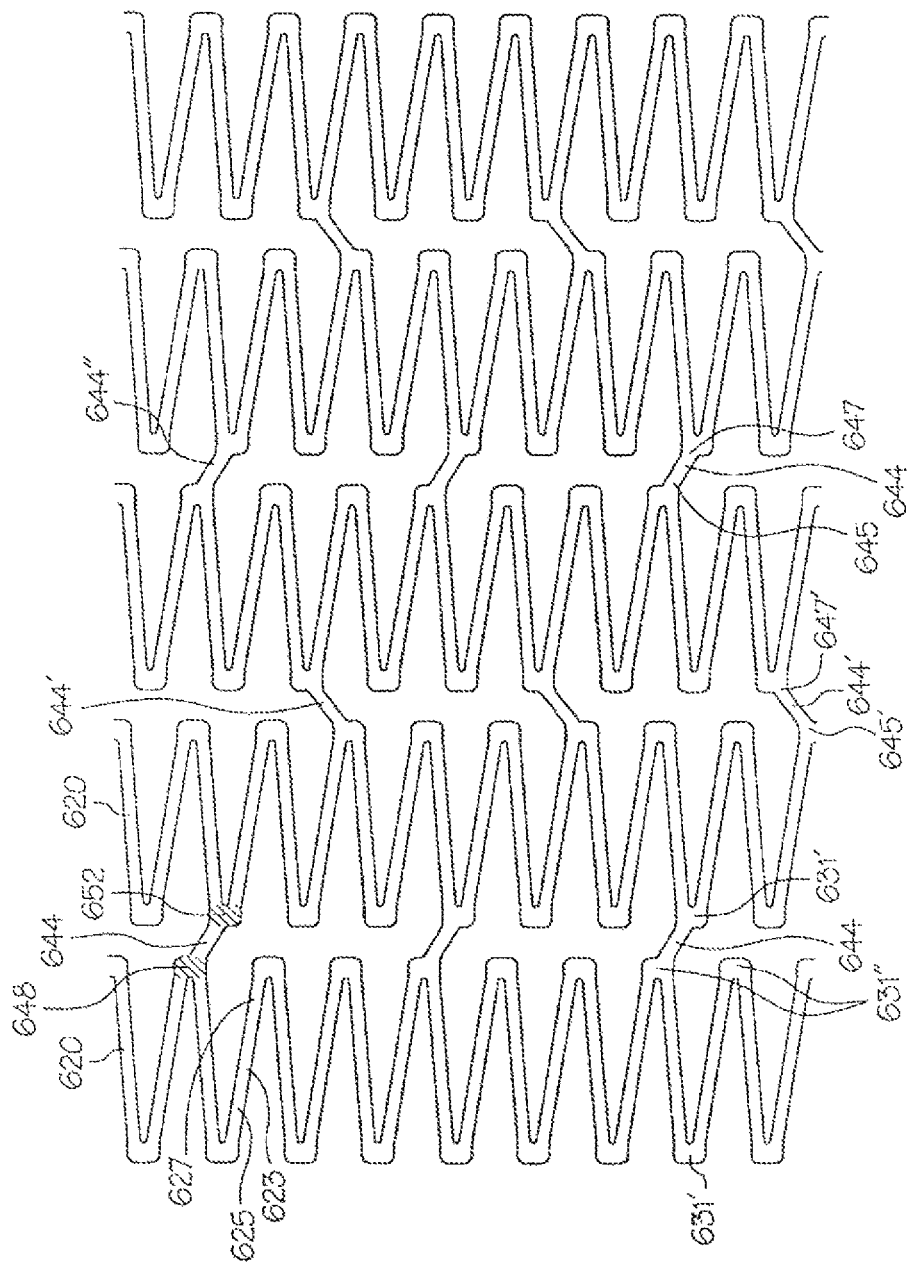
FIG. 8 shows a flat view of a stent configuration according to the invention.

This feature is also seen in the embodiment of FIG. 8 in which adjacent in-phase band-like elements 620 are interconnected by interconnecting elements 644. Interconnecting elements 644 extend at an oblique angle relative to the longitudinal axis of the stent between a peak region 648 and a trough region 652. As in FIG. 7, the orientation of interconnecting elements alternates between adjacent pairs of adjacent band-like elements. Specifically, the distal ends of interconnecting elements 644' are seen to be oriented in a counterclockwise circumferential direction along the stent relative to the proximal end of the interconnecting elements while the distal ends of interconnecting elements 644" are seen to be displaced in a clockwise circumferential direction along the stent relative to the proximal ends.

Although in the embodiments of FIGS. 2-8, adjacent bands are connected by five interconnecting elements, additional or fewer interconnecting elements may be used. Further, while interconnecting elements are shown spaced three peaks apart and three troughs apart, other separations are contemplated as well.

Figure 9:
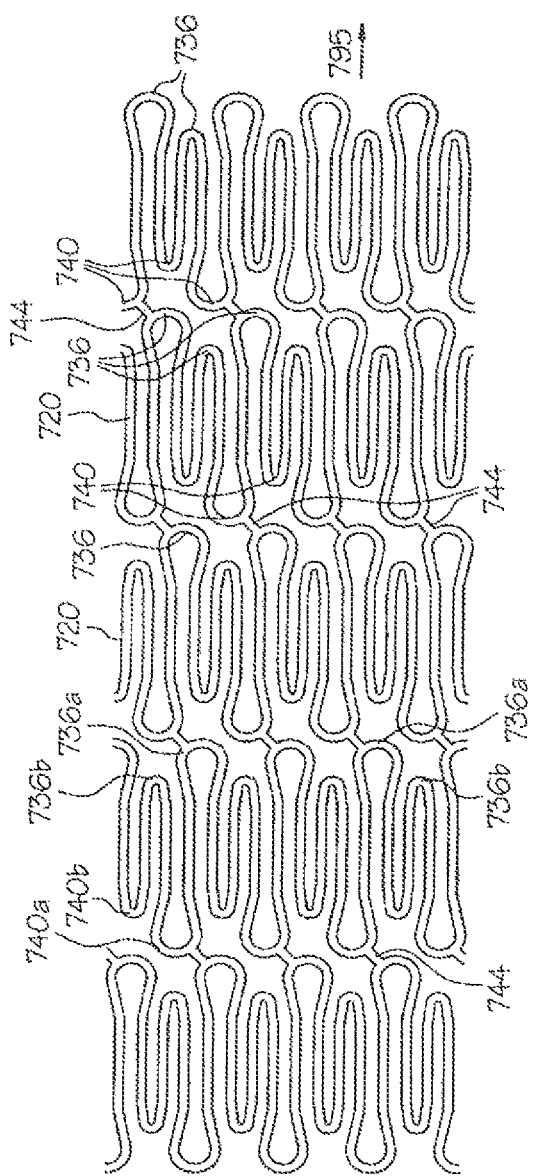
FIG. 9 shows a flat view of a stent configuration according to the invention.

In the embodiment of FIG. 9, each band-like element 720 is seen to comprise peaks 736 of more than one amplitude and troughs 740 of more than one amplitude. Large amplitude peaks 736a and small amplitude peaks 736b alternate as do large amplitude troughs 740a and small amplitude troughs 740b. As in the previous embodiments, the interconnecting elements are oriented at an oblique angle relative to the longitudinal axis 795 of the stent. More generally, the invention is directed at stents comprising band-like elements whose amplitude varies along the band-like element.

Figure 9A:
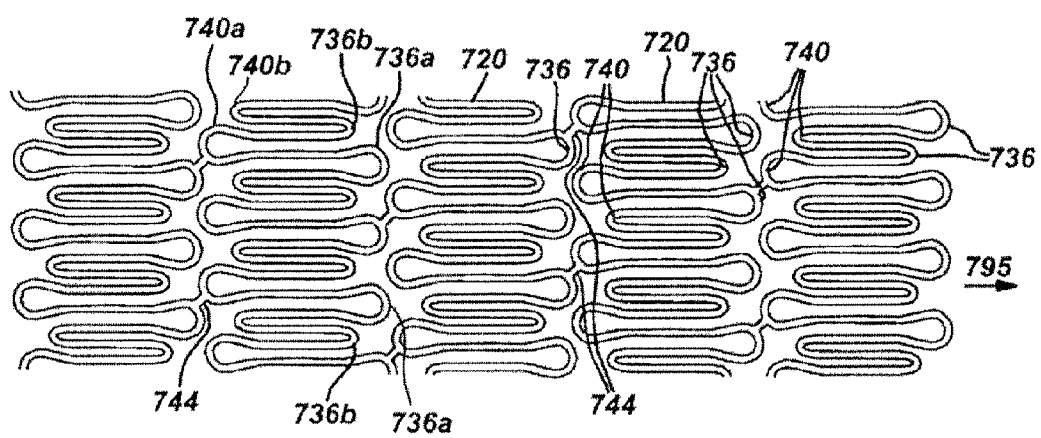
FIG. 9A shows a flat view of a stent comfiguration according to the invention.

FIG. 9A shows a further embodiment of a stent according to the invention where two interconnecting constituents 744 connect adjacent band-like elements 720 to one another. The band-like elements 720 include three-strut segments that extend in a circumferential direction between consecutive interconnecting constituents and include those struts connected by peaks 736 and troughs 740 and have a substantially S-shape. The S-shaped segments alternate with interconnecting constituents in a first helical pattern that extends along the length of the stent. The band-like elements also include circumferential segments that extend between consecutive interconnecting constituents and have five struts. These circumferential segments alternate with interconnecting constituents in a second helical pattern that extends along the length of the stent. The first and second helical patterns have opposite orientations and intersection each other.

Figure 10:
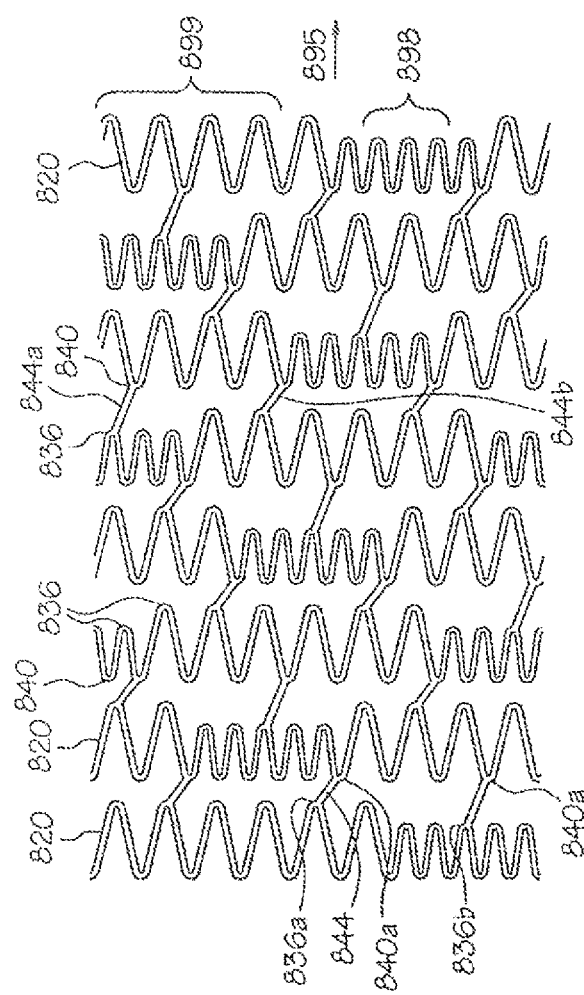
FIG. 10 shows a flat view of a stent configuration according to the invention.

In another embodiment of the invention, as shown in FIG. 10, each band-like element 820 is seen to comprise peaks 836 of more than one amplitude and troughs 840 of more than one amplitude, however, peaks of the same amplitude are grouped together within a band-like element as are troughs of the same amplitude. It is further noted that in the embodiment of FIG. 10, the location of a group of peaks of given amplitude in a band-like element varies circumferentially along the length of the stent. Interconnecting elements 844 connect peaks 836 and troughs 840 in adjacent band-like elements 820. Where several peaks of different amplitudes are present in a band-like element, the invention further contemplates the possibility of interconnecting elements extending from the large peaks 836a to large troughs 840a as in FIG. 9 as well as the possibility of interconnecting elements extending from large peaks to small troughs or from small peaks 836b to large troughs 840a as in FIG. 10. Further, the interconnecting elements between any two adjacent band-like elements may be of different lengths from one another as seen in FIG. 10 and commence at different longitudinal positions within a band-like element and terminate at different longitudinal positions within a band-like element. Interconnecting element 844a is seen to be longer than interconnecting element 844b. As in the previous embodiments, the interconnecting elements are oriented at an oblique angle relative to the longitudinal axis 895 of the stent. In the embodiment of FIG. 10, interconnecting element 844a is seen to be oriented at a smaller oblique angle relative to the longitudinal axis of the stent than interconnecting element 844b. As is apparent from FIG. 10, the invention is also directed to stents comprised of band-like elements whose wavelength varies along a given band-like element. Region 898 and region 899 of band-like element are characterized by different wavelengths.

It is also noted that in the embodiment of FIG. 10, all of the troughs 840a, b in a given band-like element 820 are aligned longitudinally along the stent and differ only in their circumferential position along the stent.

It is further noted in the embodiment of FIG. 10, the stent comprises a first group of interconnecting elements 844a and a second group of interconnecting elements 844b. The interconnecting elements of the first group are all parallel to one another and disposed at a different oblique angle relative to the longitudinal axis than the members of the second group which are all parallel to one another. As such, the invention contemplates stents having several different groups of obliquely disposed interconnecting elements where the oblique angle differs from group to group.

Figure 11:
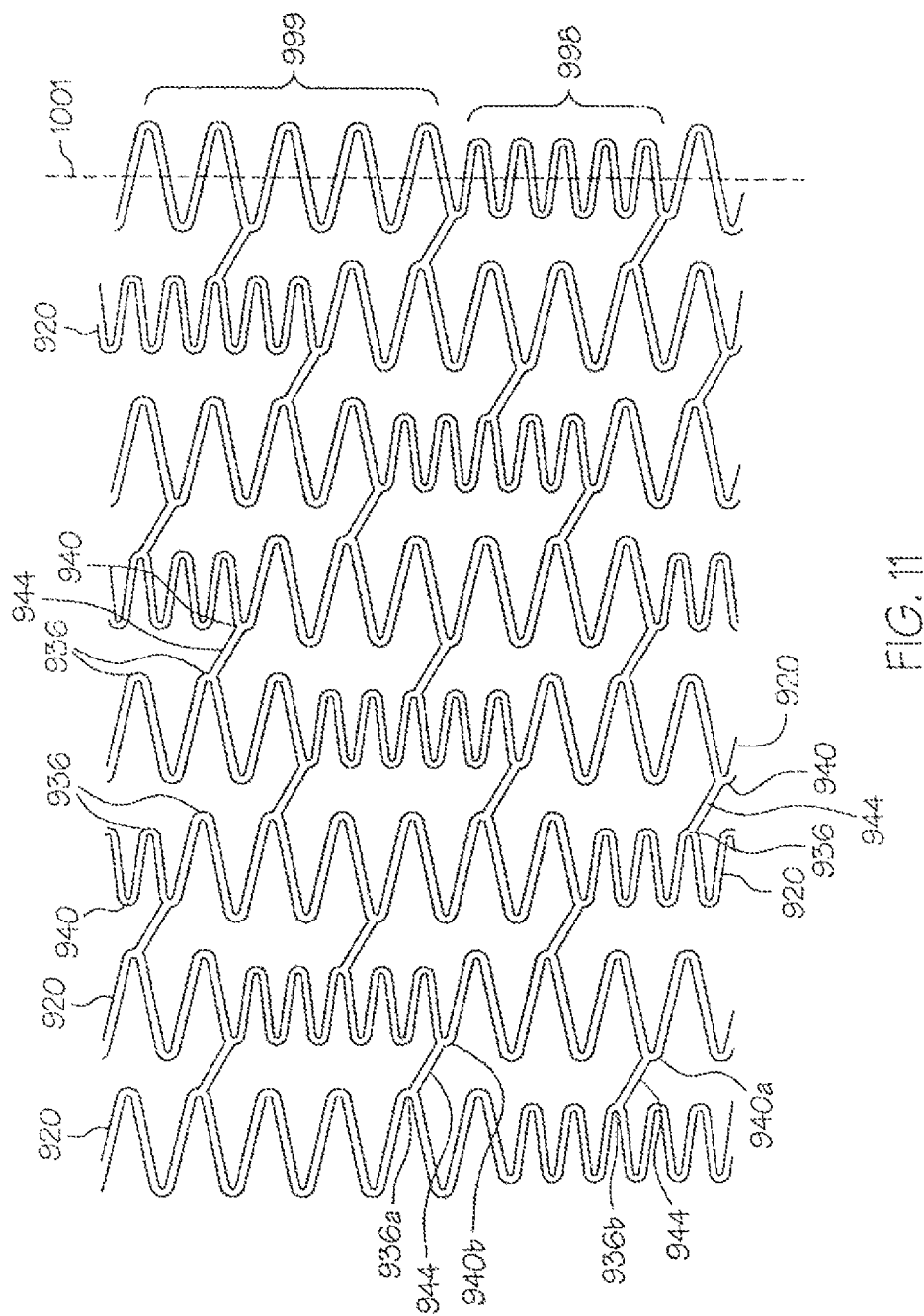
FIG. 11 shows a flat view of a stent configuration according to the invention.

In another embodiment of the invention, as shown in FIG. 11, each band-like element 920 is seen to comprise peaks 936a,b of different amplitudes and troughs 940 of different amplitudes, however, peaks of the same amplitude are grouped together within a band-like element as are troughs of the same amplitude. It is further noted that in the embodiment of FIG. 11 the location of groups of peaks of given amplitude in a band-like element varies circumferentially along the length of the stent. Interconnecting elements 944 connect large amplitude peaks 936a and small amplitude troughs 940b in adjacent band-like elements 920. Similarly, interconnecting elements 944 also connect small amplitude peaks 936b and large amplitude troughs 940a.

The invention also contemplates stents similar to that shown in FIG. 11 in which interconnecting elements extend from large peaks 936a to large troughs 940a, as in FIG. 9. Similarly, interconnecting elements may extend from small peaks 936b to small troughs 940b.

Further, the interconnecting elements between any two adjacent band-like elements may be of different lengths from one another and disposed at different oblique angles.

As is apparent from FIG. 11, the invention is also directed to stents comprised of band-like elements whose wavelength varies along a given band-like element. Region 998 and region 999 of band-like element 920 are characterized by different wavelengths.

It is also noted that in the embodiment of FIG. 11 the large amplitude portions 999 of band-like element 920 are symmetrically disposed about the center 1001 of the band-like element as are the small amplitude portions 998. The center 1001 of the band-like element is defined as a ring that runs along a path that is midway between the large peaks 936a and large troughs 940a of the band-like element. This feature may also be seen in the embodiment of FIG. 9.

The invention is also directed to a tubular, flexible, expandable stent having a longitudinal axis, comprising one or more cylindrical shaped first segments.

Cylindrical shaped first segments 20 as seen in FIG. 1, have first struts 23 having first 25 and second 27 ends. First segments 20 are defined by a member formed in an undulating pattern of interconnected paired first struts 23, in which adjacent pairs of first struts 29' and 29" in a given first segment 20 are interconnected at opposite ends 31' and 31", respectively. Adjacent segments are interconnected.

The stent may be seen more clearly in FIGS. 2-8. As shown, the stent of FIG. 3, in addition to comprising first segments 120 which are defined by an undulating pattern of interconnected paired first struts 123 in which adjacent pairs of first struts 129' and 129" in a given first segment 120 are interconnected at opposite ends 131' and 131", respectively, the stent further comprises one or more cylindrical shaped second segments 132, each second segment being defined by a member formed in an undulating pattern of interconnected paired second struts 135 and in which adjacent pairs of second struts 137' and 137" in a given second segment 132 are interconnected at opposite ends 139' and 139", respectively. First struts 123 are shorter than second struts 135. First segments 120 are formed of a number of first struts 123 and second segments 132 formed of a number of second struts 135, the number of first struts in a first segment exceeding the number of second struts in a second segment. First and second segments 120 and 132 are aligned on a common longitudinal axis 195 to define a generally tubular stent body, shown generally at 115. First and second segments 120 and 132 alternate along the stent body. Adjacent first and second segments 120 and 132 are connected by a plurality of interconnecting elements 144. Each interconnecting element 144 extends from an end 131" of paired first struts on a first segment 120 to an end 139" of paired second struts on an adjacent second segment 132. The ends of interconnecting elements 144 are circumferentially offset relative to each other.

Desirably, upon expansion of stent 115, paired struts 129" and 137" of adjacent segments 120 and 132 are displaced relative to each other about the periphery of the stent body to accommodate longitudinal flexing of the stent within the segments and without interference between adjacent segments.

In the embodiments as shown in FIGS. 4a, b, cylindrical shaped segments 220a,b are formed of interconnected struts 223a,b having first 225 and second 227 ends. Adjacent pairs of struts 229a,b' and 229a,b" in a given segment 220a,b are interconnected at opposite ends 231a,b' and 231a,b", respectively. Adjacent segments are connected by a plurality of interconnecting elements 244a,b. Each interconnecting element 244a,b extends from an end of paired struts 231a,b" on a segment to an end of paired struts 231a,b' on an adjacent segment. First end 245a,b and second end 247a,b of interconnecting elements 244a,b are seen to be circumferentially displaced along the stent.

Similar structure, denoted by similar reference numerals may be found in the stents of FIGS. 5a,b, and 6-8.

In particular, in the embodiment as shown in FIG. 8, cylindrical shaped segments 620 are formed of interconnected struts 623, having first 625 and second 627 ends. Segments 620 are defined by a member formed in an undulating pattern of interconnected paired struts 623 in which adjacent pairs of struts 629' and 629" in a given segment 620 are interconnected at opposite ends 631' and 631", respectively. Segments 620 are aligned on a common longitudinal axis 695 to define a generally tubular stent body. Adjacent segments are connected by a plurality of interconnecting elements 644 (and 644') having first 645 (645') and second 647 (647') ends, each interconnecting element 644 (644') extending from an end of paired struts 631" on a segment to an end of paired struts 631' on an adjacent segment. First end 645 (645') and second end 647 (647") are seen to be circumferentially displaced along the stent.

Figure 12:
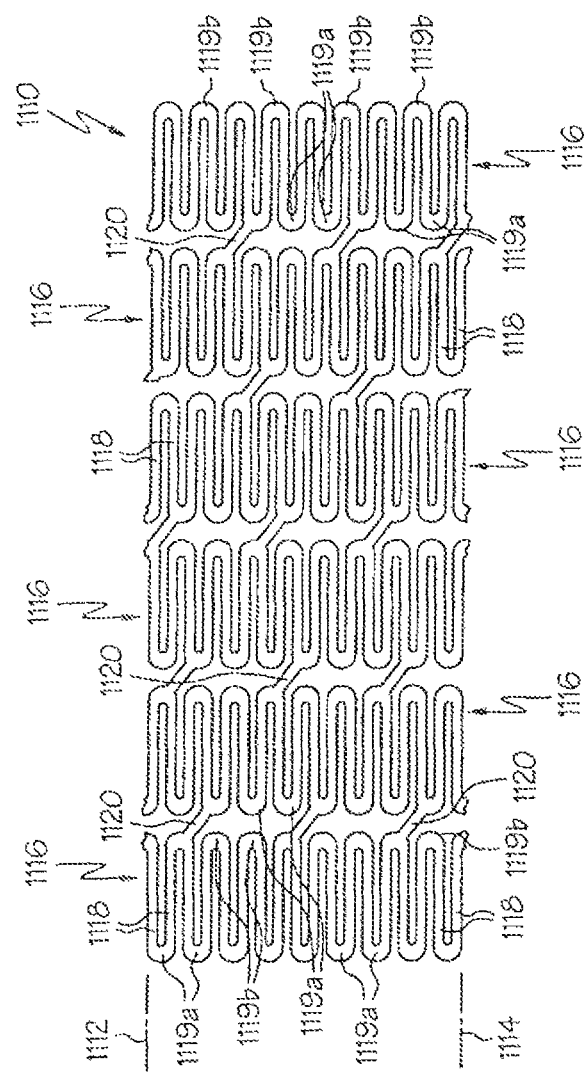
FIG. 12 shows a flat view of a stent configuration according to the invention.
Figure 13:
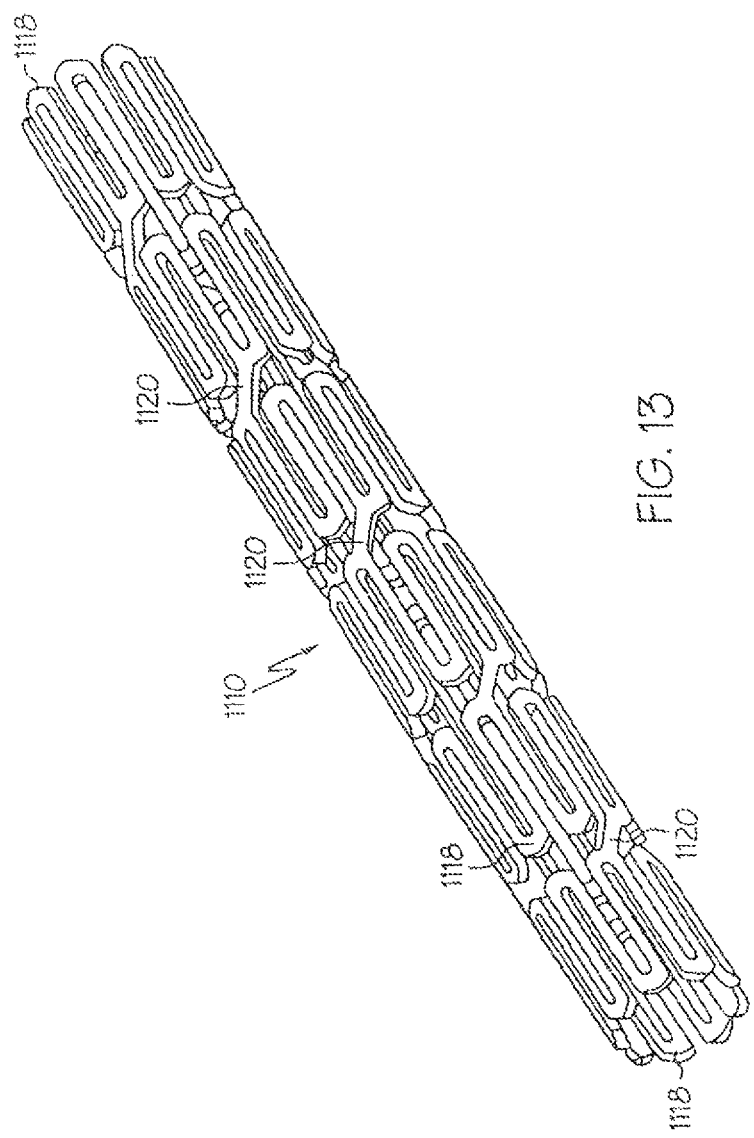
FIG. 13 shows the pattern of FIG. 12 in a tubular stent.

Additional embodiment of the stents are shown in FIGS. 12-15. FIG. 12 and FIG. 13 show a fragmentary flat view of an unexpanded stent configuration and the actual tubular stent (unexpanded), respectively. That is, the stent is shown for clarity in FIG. 12 in the flat and may be made from a flat pattern 1110 (FIG. 12) which is formed into a tubular shape by rolling the pattern so as to bring edges 1112 and 1114 together (FIG. 12). The edges may then joined as by welding or the like to provide a configuration such as that shown in FIG. 13.

The configuration can be seen in these Figures to be made up of a plurality of adjacent segments generally indicated at 1116, each of which is formed in an undulating flexible pattern of substantially parallel struts 1118. Pairs of struts are interconnected at alternating end portions 1119a and 1119b. As is seen in FIG. 12, the interconnecting end portions 1119b of one segment are positioned opposite interconnecting end portions 1119a of adjacent segments. The end portions as shown are generally elliptical but may be rounded or square or pointed or the like. Any configuration of end portions is acceptable so long as it provides an undulating pattern, as shown. When the flat form 1110 is formed into an unexpanded tube as shown in FIG. 13, the segments are cylindrical but the end portions 1119 of adjacent segments remain in an opposed position relative to each other.

A more preferred method of manufacture begins with a thin walled tube which is then laser cut to provide the desired configuration. It may also be chemically etched or EDM'd (electrical discharge machined) to form an appropriate configuration.

Interconnecting elements 1120 extend from one end portion 1119 of one segment 1116 to another end portion 1119 of another adjacent segment 1116 but not to an oppositely positioned end portion 1119 of an adjacent segment 1116. There are at least three struts included between the points on each side of a segment 1116 at which an interconnecting element 1120 contacts an end portion 1119. This results in the interconnecting elements 1120 extending in an angular direction between segments around the periphery of the tubular stent. Interconnecting elements 1120 are preferably of the same length but may vary from one segment to the other. Also, the diagonal direction may reverse from one segment to another extending upwardly in one case and downwardly in another, although all connecting elements between any pair of segments are substantially parallel. FIG. 12, for example shows them extending downwardly, right to left. Upwardly would extend up left to right in this configuration.

Figure 14:
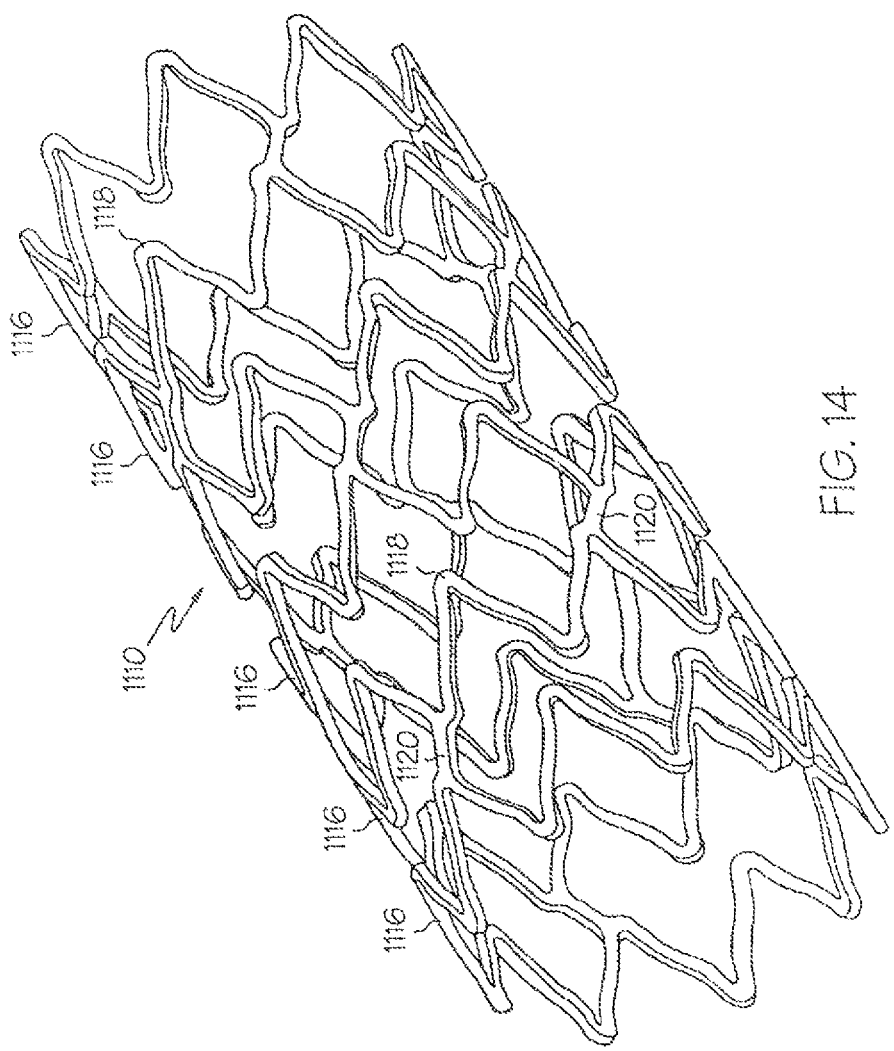
FIG. 14 shows an expanded stent of the configuration shown in FIG. 12.

As a result of this angular extension of the interconnecting elements 1120 between adjacent segments and loops, upon expansion of the stent as seen in FIG. 14, the closest adjacent end portions 1119 between segments 1116 are displaced from each other and are no longer opposite each other so as to minimize the possibility of binding or overlapping between segments, i.e., pinching.

The number of interconnecting elements 1120 may vary depending on circumstances in any particular instance. Three per segment are satisfactory for the configuration shown and at least three will be used typically.

Figure 15:
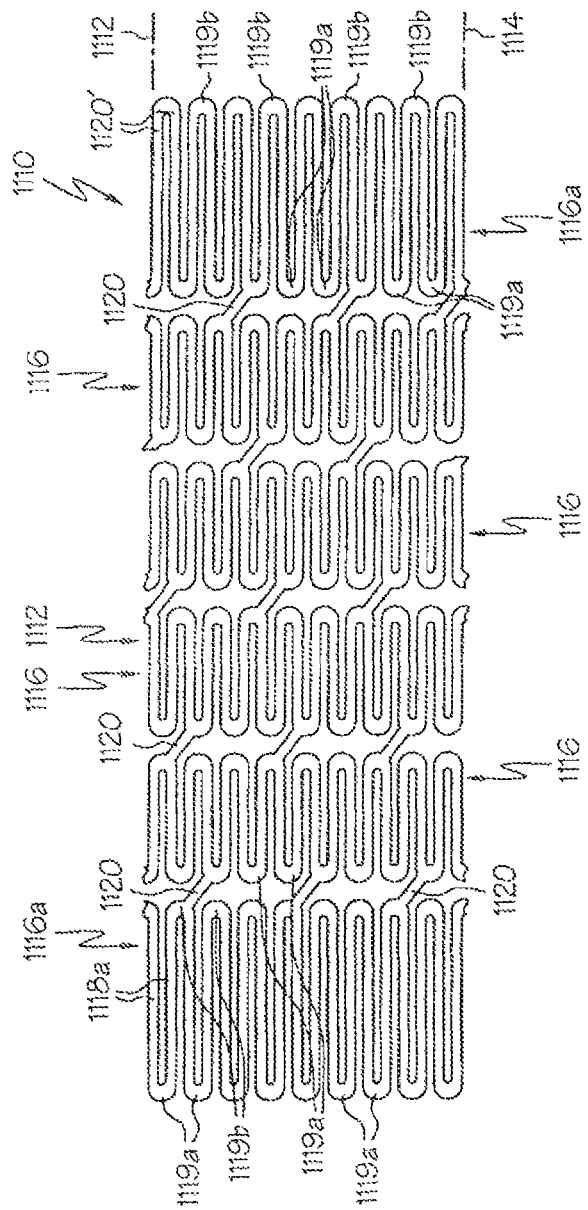
FIG. 15 shows a flat view of an alternate stent configuration according to the invention.

The alternate design shown in FIG. 15 includes longer struts 1118a in the two end segments 1116a than in the intermediate segments 1116. This allows the end segments (1116a) to have less compression resistance than the intermediate segments (1116), providing a more gradual transition from the native vessel to the support structure of the stent. Otherwise, the configuration is the same as that shown in FIG. 12.

As indicated in the Figures, the invention contemplates a variation of interconnecting element shapes ranging from rectilinear to curvilinear. The invention further contemplates embodiments in which all interconnecting elements are similarly oriented as well as embodiments in which adjacent sets of interconnecting elements extending between adjacent pairs of segments are oppositely oriented (e.g., FIGS. 7 and 8). The invention also contemplates the use of interconnecting elements which extend from a range of positions along the segments, ranging from various positions in the area in which paired struts are interconnected to other positions along the struts.

The invention also contemplates the possibility of interconnecting elements extending at an oblique angle relative to the longitudinal axis of the stent and connecting adjacent peaks and troughs on adjacent segments as well as peaks and troughs on adjacent segments which are separated by one or more peaks and/or troughs. The invention also contemplates reversing the orientation of interconnecting elements as shown in FIGS. 7 and 8.

Finally, there are preferably at least three interconnecting elements joining adjacent first and second segments although fewer or additional interconnecting elements are also contemplated.

It is understood that the peaks and troughs of the present invention need not be rounded, as shown in the Figures. The peaks and troughs may be bulbous, triangular, square, pointed, or otherwise formed of interconnected straight sections.

As already indicated, this invention is applicable to self-expanding configurations, mechanically expandable configurations and to a wide variety of materials, including both metal and plastic and any other material capable of functioning as an expandable stent. For example, the stent may be of metal wire or ribbon such as tantalum, stainless steel or the like. It may be thin-walled. It may be of shape memory alloy such as Nitinol or the like, etc. The interconnecting elements may be formed integrally with the band-like elements (or segments) or may be bonded thereto via such methods as adhesive bonding, welding or any other known method of bonding.

The above Examples and disclosure are intended to be illustrative and not exhaustive. These examples and this description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. An expandable stent having an unexpanded state, the unexpanded state consisting of:
   a plurality of cylindrical band-like elements having collinear longitudinal axes and attached to one another by a plurality of interconnecting constituents, each cylindrical band-like element consisting of a plurality of expandable circumferential segments connected to and alternating with a plurality of single substantially S-shaped portions, wherein each expandable circumferential segment extends between two consecutive interconnecting constituents and includes a quantity of curved and linear portions greater than a quantity of curved and linear portions of each substantially S-shaped portion;

first and second end segments straddling the stent;

a plurality of first expandable continuous substantially repeating paths coursing along the stent in a helical manner and consisting of a plurality of the single substantially S-shaped portions alternating with the plurality of the interconnecting constituents; and a plurality of second expandable continuous substantially repeating paths coursing along the stent in a helical manner and consisting of a plurality of the circumferential segments alternating with the plurality of the interconnecting constituents, wherein said single substantially S-shaped portions are contiguous and have a generally single S-shaped appearance, wherein said cylindrical band-like elements are contiguous patterns cylinders around the longitudinal axis, wherein said expandable circumferential segments are contiguous elements coursing in a circumferential manner about the stent.

2. The stent of claim 1, wherein the circumferential segments further comprise a plurality of segments joined together to form a repeating pattern.

3. The stent of claim 2, wherein the repeating pattern comprises a square wave form having curved peaks and valleys.

4. The stent of claim 1, wherein the plurality of circumferential segments comprise more than half of the circumference of each cylindrical band-like element.

5. The stent of claim 1, wherein each interconnecting constituent is angled with respect to the longitudinal axes.

6. The stent of claim 1, wherein the interconnecting constituent is substantially capital H-shaped.

7. The stent of claim 1, wherein at least one first repeating path crosses at least one second repeating path.

8. The stent of claim 1, wherein the curved portions of at least two adjacent cylindrical elements are circumferentially offset from one another.

9. An expandable stent consisting of:
a plurality of cylindrical band-like elements connected by a plurality of interconnecting constituents, each cylindrical band-like element comprising a plurality of expandable circumferential segments connected to a plurality of single substantially S-shaped portions, each expandable circumferential segment extending between two consecutive interconnecting constituents and including a first plurality of curved and linear portions greater than a second plurality of curved and linear portions of each substantially S-shaped portion, wherein the curved portions of at least two adjacent cylindrical band-like elements are circumferentially offset from one another;

first and second end segments straddling the stent, a plurality of first expandable continuous substantially repeating paths coursing along the stent in a helical manner and traversing substantially the entire length of the stent, each first expandable continuous substantially repeating path consisting of the single substantially S-shaped portions alternating with the interconnecting constituents, and a plurality of second expandable continuous substantially repeating paths coursing along the stent in a helical manner and traversing substantially the entire length of the stent, each second expandable continuous substantially repeating path consisting of the expandable circumferential segments alternating with the interconnecting constituents, wherein said single substantially S-shaped portions are contiguous and have a generally single S-shaped appearance, wherein said cylindrical band-like elements are contiguous patterns forming cylinders around the stent longitudinal axis, wherein said expandable circumferential segments are contiguous elements coursing in a circumferential manner about the stent.

10. The stent of claim 9, wherein the stent defines a longitudinal axis, and each interconnecting constituent is angled with respect to the longitudinal axis.

11. The stent of claim 9, wherein the interconnecting constituents are each substantially capital H-shaped.

12. The stent of claim 9, wherein at least one first repeating path crosses at least one second repeating path.

13. The stent of claim 9, wherein the stent is in an unexpanded state.

14. The stent of claim 9, wherein the stent is in an expanded state.

15. An expandable stent, consisting of:
a plurality of adjacent cylindrical rings connected by a plurality of interconnecting constituents; each cylindrical ring defined by a plurality of circumferential segments alternating with a plurality of substantially S-shaped portions, each substantially S-shaped portion having a first quantity of curved segments and linear segments, each circumferential segment defined by a portion of the stent spanning between two sequential interconnecting constituents, and each circumferential segment having a second quantity of curved segments and linear segments greater than the first quantity, wherein the curved portions of at least two adjacent cylindrical rings are circumferentially offset from one another;

first and second end segments straddling the stent;

a first continuous substantially repeating path coursing along the stent in a helical manner consisting of a plurality of the substantially S-shaped portions alternating with the plurality of the interconnecting constituents; and a second continuous substantially repeating path coursing along the stent in a helical manner and consisting of a plurality of the circumferential segments alternating with the plurality of the interconnecting constituents, wherein the first repeating path crosses the second repeating path, wherein said substantially S-shaped portions are contiguous and have a generally S-shaped appearance, wherein said cylindrical rings are contiguous patterns forming cylinders around the stent longitudinal axis, wherein said circumferential segments are contiguous elements coursing in a circumferential manner about the stent.

16. The stent of claim 15, wherein the stent is in an unexpanded state.

17. The stent of claim 15, wherein the stent is in an expanded state.

18. An expandable stent, consisting of:
first and second end segments straddling the stent; and
a plurality of adjacent cylindrical band-like elements connected to one another by a plurality of interconnecting constituents;
each cylindrical band-like element including a plurality of first expandable circumferential segments, each first expandable circumferential segment extending between exactly two interconnecting constituents and consisting of five linear segments connected to each other by curved portions;
each cylindrical band-like element including a plurality of expandable second circumferential segments, each expandable second circumferential segment extending between exactly two interconnecting constituents and consisting of three linear segments connected to each other by curved portions;
the first and second expandable circumferential segments alternating with one another in each cylindrical band-like element,
wherein the curved portions of the first and second expandable circumferential segments of a first cylindrical band-like element are not aligned with the curved portions of the first and second circumferential segments of an adjacent cylindrical band-like element;
wherein the expandable first circumferential segments of adjacent cylindrical band-like elements form a first continuous substantially repeating path coursing along the stent in a helical manner and consisting of a plurality of the first expandable circumferential segments alternating with the plurality of the interconnecting constituents;
wherein the second expandable circumferential segments of adjacent cylindrical band-like elements form a second continuous substantially repeating path coursing along the stent in a helical manner and consisting of a plurality of the second expandable circumferential segments alternating with the plurality of the interconnecting constituents;
wherein the cylindrical band-like elements are contiguous patterns forming cylinders around the stent longitudinal axis;
wherein the expandable first and second circumferential segments are contiguous elements coursing in a circumferential manner about the stent.

19. The expendable stent of claim 18, wherein each interconnecting constituent defines a substantially linear strut angled with respect to a longitudinal axis of the stent.

20. The expandable stent of claim 18, wherein the stent is in an unexpanded state.

21. The expandable stent of claim 18, wherein the second expandable circumferential segments are each substantially S-shaped.

22. An expandable stent having an unexpanded state, the unexpanded state consisting of:
a plurality of band-like elements having collinear longitudinal axes and attached to one another by a plurality of interconnecting elements,
each band-like element consisting of a plurality of first expandable groups including peaks and troughs and a plurality of second expandable groups including peaks and troughs, each second expandable group forming a single substantially S-shaped portion, each first expandable group connected to and alternating with each single substantially S-shaped portion,
wherein each first expandable group extends between two consecutive interconnecting elements and includes a quantity of curved and linear portions greater than a quantity of curved and linear portions of each single substantially S-shaped portion;
first and second end segments straddling the stent;
a plurality of first expandable paths extending between the proximal end of the stent and the distal end of the stent in a helical manner and consisting of a plurality of the single substantially S-shaped portions alternating with the plurality of the interconnecting elements; and
a plurality of second expandable paths extending between the proximal end of the stent and the distal end of the stent in a helical manner and consisting of a plurality of the first expandable groups alternating with the plurality of the interconnecting elements,
wherein each single substantially S-shaped portion is contiguous and has a generally single S-shaped appearance,
wherein each band-like element is a contiguous pattern forming a cylinder around the longitudinal axis,
wherein each first expandable group is a contiguous element coursing in a circumferential manner about the stent.

23. The stent of claim 22, wherein the first expandable groups further comprise a plurality of segments joined together to form a repeating pattern.

24. The stent of claim 23, wherein the repeating pattern comprises an undulating wave form having curved peaks and troughs.

25. The stent of claim 22 wherein the plurality of the first expandable groups comprise more than half of the circumference of each band-like element.

26. The stent of claim 22, wherein each interconnecting element is angled with respect to the longitudinal axes.

27. The stent of claim 22, wherein the interconnecting element is substantially rectilinear.

28. The stent of claim 22, wherein at least one said first path extending between the proximal end of the stent and the distal end of the stent crosses at least one said second path extending between the proximal end of the stent and the distal end of the stent.

29. The stent of claim 22, wherein the curved portions of at least two adjacent band-like elements are out of phase with one another.

30. The stent of claim 22, wherein the curved portions of peaks and troughs of at least two adjacent band-like elements are circumferentially displaced from one another.

* * * * *